(12) United States Patent
Wheeler et al.

(10) Patent No.: US 11,065,195 B2
(45) Date of Patent: *Jul. 20, 2021

(54) TOPICAL COMPOSITION

(71) Applicant: MC2 THERAPEUTICS LIMITED, Leatherhead (GB)

(72) Inventors: Derek Wheeler, Leatherhead (GB); David F. Steele, Leatherhead (GB); Michelle Georgiou, Leatherhead (GB); Steen Sindet-Pedersen, Leatherhead (GB)

(73) Assignee: MC2 Therapeutics Limited, Leatherhead (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/287,779

(22) Filed: Feb. 27, 2019

(65) Prior Publication Data
US 2019/0358151 A1    Nov. 28, 2019

Related U.S. Application Data

(63) Continuation of application No. 12/076,248, filed on Mar. 14, 2008, now Pat. No. 10,265,265, which is a
(Continued)

(30) Foreign Application Priority Data

Mar. 15, 2007  (EP) ..................... 07251094
Dec. 4, 2007   (GB) ..................... 0723728

(51) Int. Cl.
*A61K 9/00*    (2006.01)
*A61K 31/573*  (2006.01)
(Continued)

(52) U.S. Cl.
CPC .......... *A61K 9/0014* (2013.01); *A61K 31/573* (2013.01); *A61K 31/59* (2013.01);
(Continued)

(58) Field of Classification Search
CPC .... A61K 9/0014; A61K 31/573; A61K 31/59; A61K 45/06; A61K 47/06
See application file for complete search history.

(56) References Cited

U.S. PATENT DOCUMENTS 4,486,333 A   12/1984  Sebba
4,533,546 A    8/1985  Kishi et al.
(Continued)

FOREIGN PATENT DOCUMENTS

CN   1351499 A    5/2002
CN   1832731 A    9/2006
(Continued)

OTHER PUBLICATIONS

"Adams, "Vitamin D mythes, facts and statistics," Natural News, 2005, Abstract.".
(Continued)

*Primary Examiner* — San Ming R Hui
(74) *Attorney, Agent, or Firm* — Merchant & Gould P.C.

(57) ABSTRACT

A composition suitable for topical application comprising a continuous phase and at least one discontinuous phase, said composition comprising at least one polyaphron dispersion, at least one vitamin D or vitamin D analogue and at least one corticosteroid.

19 Claims, 2 Drawing Sheets

Figure 1:
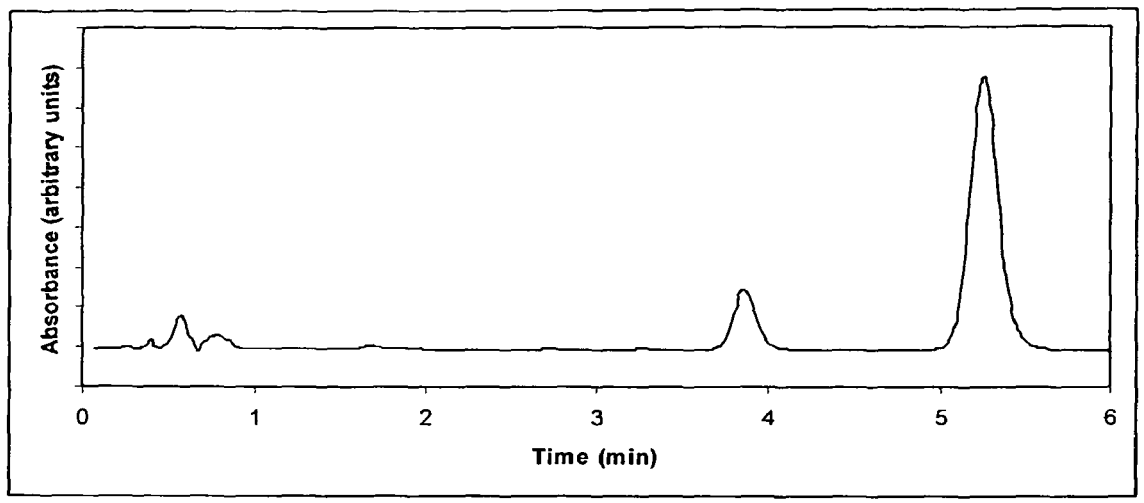

Related U.S. Application Data continuation-in-part of application No. 11/905,163, filed on Sep. 27, 2007.

(51) Int. Cl.
  *A61K 31/59* (2006.01)
  *A61K 45/06* (2006.01)
  *A61K 47/06* (2006.01)
  *A61K 47/10* (2017.01)
  *A61K 47/44* (2017.01)

(52) U.S. Cl.
  CPC ............. *A61K 45/06* (2013.01); *A61K 47/06* (2013.01); *A61K 47/10* (2013.01); *A61K 47/44* (2013.01)

(56) References Cited

U.S. PATENT DOCUMENTS

| | | | |
|---|---|---|---|
| 4,871,723 A | 10/1989 | Makino et al. | |
| 4,900,552 A | 2/1990 | Sanvordeker et al. | |
| 4,936,933 A | 6/1990 | Yabsley et al. | |
| 4,944,938 A | 7/1990 | Potini | |
| 4,999,198 A | 3/1991 | Barnett et al. | |
| 5,185,150 A | 2/1993 | DeLuca et al. | |
| 5,474,979 A | 12/1995 | Ding et al. | |
| 5,549,888 A | 8/1996 | Venkateswaran | |
| 5,573,757 A | 11/1996 | Riess et al. | |
| 5,645,856 A | 7/1997 | Lacy et al. | |
| 5,660,858 A | 8/1997 | Parikh et al. | |
| 5,763,426 A | 6/1998 | Hansen et al. | |
| 5,840,881 A | 11/1998 | Uda et al. | |
| 5,952,383 A | 9/1999 | Metziger et al. | |
| 5,955,097 A | 9/1999 | Tapolsky et al. | |
| 5,990,100 A | 11/1999 | Rosenberg et al. | |
| 6,096,338 A | 8/2000 | Lacy et al. | |
| 6,165,479 A | 12/2000 | Wheeler | |
| 6,200,581 B1 | 3/2001 | Lin et al. | |
| 6,238,678 B1 | 5/2001 | Oblong et al. | |
| 6,538,039 B2 | 3/2003 | Laurent | |
| 6,562,370 B2 | 5/2003 | Luo et al. | |
| 6,585,997 B2 | 7/2003 | Moro et al. | |
| 6,599,527 B1 | 7/2003 | Leigh et al. | |
| 6,753,013 B1 * | 6/2004 | Didriksen | A61K 47/10 424/484 |
| 6,787,529 B2 | 9/2004 | Hoy et al. | |
| 7,001,607 B1 | 2/2006 | Menz et al. | |
| RE39,706 E | 6/2007 | Hansen et al. | |
| 7,709,431 B2 | 5/2010 | Mercurio et al. | |
| 8,263,580 B2 | 9/2012 | Buchta et al. | |
| 8,298,515 B2 | 10/2012 | Buchta et al. | |
| 8,501,712 B2 | 8/2013 | Baker et al. | |
| 8,574,563 B2 | 11/2013 | Bachand et al. | |
| 8,629,111 B2 | 1/2014 | Acheampong et al. | |
| 8,629,128 B2 | 1/2014 | Buchta | |
| 8,633,162 B2 | 1/2014 | Acheampong et al. | |
| 8,642,556 B2 | 2/2014 | Acheampong et al. | |
| 8,648,008 B2 | 2/2014 | Misra et al. | |
| 9,549,896 B2 | 1/2017 | Crutchley | |
| 9,610,245 B2 | 4/2017 | Steele | |
| 10,154,959 B1 | 12/2018 | Steele | |
| 2005/0001643 A1 | 1/2005 | Yoshida et al. | |
| 2005/0002546 A1 | 1/2005 | Florent et al. | |
| 2005/0020546 A1 | 1/2005 | Laidlaw et al. | |
| 2005/0026877 A1 | 2/2005 | Chen et al. | |
| 2005/0082515 A1 | 4/2005 | Masuichi et al. | |
| 2005/0147658 A1 | 7/2005 | Tapolsky et al. | |
| 2005/0232869 A1 | 10/2005 | Tamarkin et al. | |
| 2005/0238676 A1 | 10/2005 | Gladman et al. | |
| 2005/0249757 A1 | 11/2005 | Kannan et al. | |
| 2005/0281749 A1 | 12/2005 | Willcox et al. | |
| 2005/0281750 A1 | 12/2005 | Willcox et al. | |
| 2005/0281754 A1 | 12/2005 | Willcox et al. | |
| 2005/0281755 A1 | 12/2005 | Zarif et al. | |
| 2005/0281848 A1 | 12/2005 | Zanutto et al. | |
| 2005/0281850 A1 | 12/2005 | Zanutto et al. | |
| 2005/0282788 A1 | 12/2005 | Zanutto et al. | |
| 2005/0282792 A1 | 12/2005 | Andres | |
| 2006/0147383 A1 | 7/2006 | Mallard et al. | |
| 2006/0188576 A1 | 8/2006 | Takruri | |
| 2006/0228408 A1 | 10/2006 | Charman et al. | |
| 2006/0239947 A1 | 10/2006 | Dias et al. | |
| 2006/0292080 A1 | 12/2006 | Abram et al. | |
| 2007/0041910 A1 | 2/2007 | Pitre et al. | |
| 2007/0048369 A1 | 3/2007 | Foreman et al. | |
| 2007/0059346 A1 | 3/2007 | Maibach | |
| 2007/0190088 A1 | 8/2007 | Childs et al. | |
| 2007/0207192 A1 | 9/2007 | Holl et al. | |
| 2007/0276004 A1 | 11/2007 | Hirsch et al. | |
| 2008/0207570 A1 | 8/2008 | Segura-Orsoni | |
| 2008/0227759 A1 | 9/2008 | Wheeler et al. | |
| 2008/0234239 A1 | 9/2008 | Wheeler et al. | |
| 2008/0254105 A1 | 10/2008 | Tapolsky et al. | |
| 2009/0113031 A1 | 4/2009 | Ruan et al. | |
| 2009/0137523 A1 | 5/2009 | Shin et al. | |
| 2009/0221625 A1 | 9/2009 | Hirsch et al. | |
| 2010/0062975 A1 | 3/2010 | Houck | |
| 2010/0279951 A1 | 11/2010 | Morgan et al. | |
| 2011/0201639 A1 | 8/2011 | Skak et al. | |
| 2012/0184511 A1 | 7/2012 | Goebel | |
| 2013/0101525 A1 | 4/2013 | Buchta | |
| 2016/0318955 A1 | 11/2016 | Akama | |
| 2019/0060288 A1 | 2/2019 | Crutchley | |

FOREIGN PATENT DOCUMENTS

| | | |
|---|---|---|
| EP | 0474126 A1 | 3/1992 |
| EP | 0474517 A2 | 3/1992 |
| EP | 0679154 A1 | 11/1995 |
| EP | 0679392 A1 | 11/1995 |
| EP | 0799620 A1 | 10/1997 |
| EP | 0884995 A1 | 12/1998 |
| EP | 1039893 A1 | 10/2000 |
| EP | 1178808 A1 | 2/2002 |
| EP | 1093371 B1 | 5/2005 |
| EP | 1575542 A1 | 9/2005 |
| EP | 1641463 A1 | 4/2006 |
| EP | 1686972 A1 | 8/2006 |
| EP | 1758586 A1 | 3/2007 |
| EP | 1758587 A1 | 3/2007 |
| EP | 1758588 A1 | 3/2007 |
| EP | 1758589 A1 | 3/2007 |
| EP | 1758591 A1 | 3/2007 |
| EP | 1765356 A1 | 3/2007 |
| EP | 1771180 A1 | 4/2007 |
| EP | 1778185 A1 | 5/2007 |
| EP | 1331927 B1 | 12/2007 |
| EP | 1970047 A1 | 9/2008 |
| EP | 1970048 A1 | 9/2008 |
| EP | 1970049 A1 | 9/2008 |
| EP | 2308468 A1 | 4/2011 |
| EP | 2596788 A1 | 5/2013 |
| JP | 62135417 A | 6/1987 |
| JP | 10-139669 A | 5/1998 |
| JP | 2005325140 A | 11/2005 |
| RU | 2238734 C2 | 10/2004 |
| RU | 2276177 C2 | 9/2010 |
| WO | 9531211 A1 | 11/1995 |
| WO | 9600074 A1 | 1/1996 |
| WO | 9625923 A1 | 8/1996 |
| WO | 9732559 A1 | 9/1997 |
| WO | 9955312 A2 | 11/1999 |
| WO | 0064450 A1 | 11/2000 |
| WO | 0162214 A1 | 8/2001 |
| WO | 0204570 A2 | 1/2002 |
| WO | 0234235 A1 | 5/2002 |
| WO | 03/064024 A1 | 8/2003 |
| WO | 2004041227 A1 | 5/2004 |
| WO | 2005001643 A2 | 1/2005 |
| WO | 2005011628 A2 | 2/2005 |
| WO | 2005011643 A1 | 2/2005 |
| WO | 2005016321 A1 | 2/2005 |
| WO | 2005061321 A2 | 7/2005 |
| WO | 2005082515 A2 | 9/2005 |

(56) References Cited

FOREIGN PATENT DOCUMENTS

| WO | 2006050836 A2 | 5/2006 |
|---|---|---|
| WO | 2006/062334 A1 | 6/2006 |
| WO | 2006/099390 A1 | 9/2006 |
| WO | 2006111426 A1 | 10/2006 |
| WO | 2008/110826 A1 | 9/2008 |
| WO | 2008110815 A1 | 9/2008 |
| WO | 2009/001092 A1 | 12/2008 |
| WO | 2009/001099 A2 | 12/2008 |
| WO | 2009001099 A2 | 12/2008 |
| WO | 2009007409 A2 | 1/2009 |
| WO | 2009071594 A1 | 6/2009 |
| WO | 2009/090495 A1 | 7/2009 |
| WO | 2010120838 A1 | 10/2010 |
| WO | 2010124096 A1 | 10/2010 |
| WO | 2010141591 A1 | 12/2010 |
| WO | 2011154004 A1 | 12/2011 |
| WO | 2017/093857 A1 | 6/2017 |

OTHER PUBLICATIONS

"Ashcroft et al., "Systematic Review . . . Plaque Psoriasis" British Medical Journal, 320:963-967 (2000).".
"Office Action for Chinese Patent Application No. 200880008496.X (with English translation) (11 pages).".
"EP 11158099.9 Search Report dated Sep. 27, 2011.".
"Charakida et al., "Calcipotriolbetamethasone dipropionate for the treatment of psoriasis," Expert Opin. Pharmacother, 7(5):597-606 (2006)".
"EP Application No. 1196067.0 Ryttov Declaration (4 pages).".
"EP Application No. 11196069.6 Response filed Aug. 8, 2013 (93 pages).".
"Farines et al., "Analysis of the triglycerides of some vegetable oils," Journal of Chemical Education, 65(5):464-466 (1988).".
"Final Report on the safety assessmnet of peanut (*Arachis hypogaea*) oil etc. International Journal of Toxicology, 20(2):65-77 (2001).".
"Guenther et al., "Efficacy and safety of a new combination of calcipotriol and betamethasone dipropionate (once or twice daily) compared to calcipotriol (twice daily) in the treatment of psoriasis vulgaris: a randomized, double-blind, vehicle-controlled clinical trial," British Journal of Dermatology, 147:316-323 (2002).".
"Kaufmann et al., "A New CalciptriolBetamethasone Dipropionate Formulation (DaivobetTM) is an Effective Once-Daily Treatment for Psoriasis vulgaris," Dermatology, 205:389-393 (2005).".
"Kim et al., "Lipolysis of Corn, peanut and randomized peanut oils," Lipids, 18(11):842-844 (1983).".
"Kragballe, "Treatment of psoriasis with calcipotriol and other vitamin D analogues," Journal of the American Academy of Dermatology, Dec. 1992, vol. 27, Issue 6, part 1 (Abstract only).".
"Kragballe et al., "Efficacy of once-daily treatment regimens wit calcipotriolbetamethasone dipropionate ointment and calcipotriol ointment in psoriasis vulgaris," British Journal of Dermatology, 150:1167-1173 (2004).".
"Lebwohl, "The Evolution of Vitamin D Analogues for the Treatment of Psoriasis," Arch. Dermatol., 131:1323-1324 (1995).".
"Montalto, Jr., "A Study of the Feasibility of Polyaphrons as Trasdermal Drug Delivery Systems," MS thesis; University of Rhode Island, Kingston, 1984, Print (95 pages).".
"Ortonne et al., "Efficacy of treatment with calcipotriolbetamethasone dipropionate followed by calcipotriol alone compared with tacalcitol for the treatment of psoriasis vaulgaris: a randomized, doubl-blind trial," Dermatology, 2004209(4):308-313 (2004) PMID U.S. Appl. No. 15/539,894, Medline, DA filed Nov. 12, 2004.".
"PCT/EP2012/054498 International Search Report dated May 7, 2012.".
"PCT/GB2004/003329 International Search Report dated Feb. 16, 2005.".
"Poyner et al., "Long Term Treatment of Chronic Plaque Psoriasis with Calcipotriol" Journal of Dermatological Treatment, 4(4):173-177 (1993).".

"Russian Patent Application No. 2009138045 Office Action (with English translation).".
"Sebba, "Preparation and Properties of Polyaphrons (Biliquid Foams)" Chemistry and Industry, Chemical Society, Letchworth, GB, No. 10, 1984, pp. 367-372.".
"Traulsen et al., "The Atrophogenic Potential and Dermal Tolerance of CalcipotriolBetamethasone Dipropionate Ointment Compared with Betamethasone Dipropionate Ointment," Dermatology, 207: 166-172 (2003).".
"U.S. Office Action cited in U.S. Appl. No. 14/003,871 dated Jun. 24, 2015.".
"U.S. Office Action cited in U.S. Appl. No. 12/450,183 dated Aug. 26, 2015.".
"Van De Kerkhol et al., "A two-compound product containing calcipotriol and betamethasone dipropionate provides rapid, effective treatment of psoriasis vulgaris regardless of baseline disease severity", Dermatology, 210 (4):294-299 (2005) (Abstract).".
"Van De Kerkhol et al., "Mixed treatment comparison of a two-compound formulation (TCF) product containing calcipotriol and betamethasone dipropionate with other topical treatments in psoriasis vulgaris," Current Medical Research & Opinion, 27(1):225-238 (2011).".
"Wheeler, "High Internal Phase Dispersions," Conference: Cosmetics and Coloids (online) Feb. 15, 2005, pp. 1-12.".
"CapricCaprylic Triglyceride vs. Fractionated Coconut Oil, from http:chemicaloftheday.squarespace.comqa201528capriccaprylic-triglyceride-vs-fractionated-coconut-oil.html, pp. 1-6, accessed Jun. 12, 2015".
"Gelatine, from http:www.gelita.comsolutions-and-productsgelatine-gelling-agent-numerous-applications, p. 1, accessed Jun. 13, 2015".
"Eyedrops Medical Definition, from http:www.merriam-webster. commedicaleyedrops, p. 1, accessed Dec. 24, 2015".
"Decision of Court of Appeals for Federal circuit, Leo Pharmaceutical Products, Ltd. Appelle, 2012-1520, Appeal from BPAI No. 95/000,153, decided Aug. 12, 2013".
"Le Yan (Stability, Transport, and Applications of polyaphrons in poromedia, A dissertation Submitted to the Graduate Faculty of the Louisianna State University and Agricultural and Mechanical College in Partial fulfillment of the Requirements for the degree of Doctor of Philosophy, May 2005)".
"Rathore et al., An Insight into Ophthalmic Drug Delivery System, International Journal of Pharmaceutical Sciences and Drug Research, 2009, pp. 1-5".
"Patel et al., Ophthalmic Drug Delivery System—A Review, Der Pharmacia Lettre, 2010, 2, pp. 100-115, published Feb. 4, 2010".
"Lye et al. "Immobilization of Candida cylindracea Lipase on Colloidal Liquid Aphrons (CLAs) and Development of a ContinuoCLA-Membrane Reactor," Biotechnology and Bioengineering, vol. 51, pp. 69-78 (1996)".
"Stuckey et al. The Immobilisation of Enzymes on Colloidal Liquid Aphrons (CLAs) for Bi-phasic Reactions: Stability, Protein Structure, and use in Crossflow Membrane Bioreactors".
"T.J. Lin:" Surfactant Location and Required HLB"; J. Soc. Cosmet. Chem., 21 (1970), pp. 365-375".
Crutchley, "The Encapsulation of Oils and Oil Soluble Substances Within Polymer Films", PhD Thesis, The University of Leeds (2006).
First Examination Report from Indian Application No. 201947029785, dated Jan. 24, 2020.
First Examination Report from Indian Patent Application No. 20184 7040549, dated Nov. 25, 2019.
G. Godwin, Harry's Cosmeticology 7th Edition (1982).
Hicks, "Investigating the Generation, Characterisation Structure of Biliquid Foams", PhD Thesis, University of Bristol (2005).
International Preliminary Report on Patenatbility for PCT/EP2017/057897, dated Oct. 9, 2018.
International Preliminary Report on Patenatbility for PCT/GB2018/050263 dated Aug. 15, 2019.
International Search Report and Written Opinion for PCT/EP2017/057897 dated Jun. 8, 2017.
International Search Report and Written Opinion for PCT/GB2018/050263 dated Apr. 9, 2018.

(56) References Cited

OTHER PUBLICATIONS

Jay Araman et al., "Topical Delivery of Erythromycin from Various Formulations: An In Vivo Hairless Mouse Study", Journal of Pharmaceutical Sciences (1996) vol. 85(10): 1082-1084.
L. Eichenfield, "Long-term safety of crisaborole topical ointment, 2%, in atopic dermatitis", Journal of Investigative Dermatology, vol. 136 (5): S49.
Lye and Stuckey, "Structure and stability of colloidal liquid aphrons," Colloid and Surfaces, 131, 119-136 (1998).
Mollison et al., "A macrolactam inhibitor of T helper type 1 and T helper type 2 cytokine biosynthesis for topical treatment of inflammatory skin diseases", J Invest Dermatol., 112(5):729-38 (1999).
Search Report for British Patent Application No. 1701583.5, dated Oct. 25, 2017.
Search Report for European Patent Application No. 16163724.4, dated Sep. 19, 2016.
Sebba, "Biliquid Foams—A Preliminary Report", J. Colloid and Interface Science, 40:2, 468-474 (1972).
Sebba, "The Behaviour of Minute Oil Droplets Encapsulated in a Water Film", Colloid Polymer Sciences, 257, 392-396 (1979).
T. Akama et al., "Discovery and structure-activity study of a novel benzoxaborole anti-inflammatory agent (AN2728) for the potential topical treatment of psoriasis and atopic dermatitis", Bioorganic & Medicinal Chemistry Letters vol. 19 (8) (2009).
Yamanaka et al., "Development and evaluation of a tacrolimus cream formulation using a binary solvent system", International Journal of Pharmaceuticals, (2014).
U.S. Appl. No. 16/090,993, filed Oct. 3, 2018 (Exhibit A).
U.S. Appl. No. 16/482,177, filed Jul. 30, 2019 (Exhibit B).

\* cited by examiner

TOPICAL COMPOSITION

CROSS-REFERENCE TO RELATED APPLICATIONS

This application is a continuation of U.S. patent application Ser. No. 12/076,248, filed Mar. 14, 2008, and granted as U.S. Pat. No. 10,265,265 on Apr. 23, 2019. U.S. patent application Ser. No. 12/076,248 is a continuation-in-part of U.S. patent application Ser. No. 11/905,163, filed Sep. 27, 2007, and claims priority to European Application 07251094.4, filed Mar. 15, 2007 and Great Britain Application 0723728-2, filed Dec. 4, 2007, to the extent appropriate. U.S. patent application Ser. No. 12/076,248, U.S. patent application Ser. No. 11/905,163, European Application 07251094.4, and Great Britain Application 0723728-2 are incorporated by reference.

BACKGROUND OF THE INVENTION

Field of the Invention

The present invention relates to a composition for topical application comprising at least one vitamin D or vitamin D analogue and at least one corticosteroid.

The Prior Art

It is known for compositions comprising vitamin D or vitamin D analogues to be used for the treatment of a number of skin conditions.

For example, EP-B-474,517 discloses the use of compositions containing one or more 1a-hydroxylated-19-nor vitamin D compounds with a triple bond in the side chain in the treatment of psoriasis.

U.S. Pat. No. 4,871,723 discloses a process for treating psoriasis by topically applying a composition comprising vitamin D and a wax carrier. Specifically, U.S. Pat. No. 4,871,723 discloses a composition comprising a) a pharmaceutically effective amount of an active-type vitamin D3, b) a solvent selected from fatty acid esters, higher alcohols with 10 or more carbons and propylene carbonate and c) an oily carrier selected from white vaseline, yellow vaseline and liquid paraffin.

U.S. Application Publication 2005/0020546 A1 discloses a pharmaceutical composition comprising an active vitamin D compound in emulsion pre-concentrate formulations, as well as emulsions and sub-micron droplet emulsions produced therefrom. In particular, the pharmaceutical compositions of U.S. Application Publication 2005/0020546 A1 comprise
 (a) a lipophilic phase component;
 (b) one or more surfactants; and
 (c) an active vitamin D compound.

The surfactant or surfactants are suitably present in an amount of 1% to 90% by weight based on the total weight of the composition, and preferably from about 5% to about 85% by weight based on the total weight of the composition.

Presently available compositions contain relatively high concentrations of vitamin D or vitamin D analogues and surfactants which often lead to skin irritation and worsening of psoriasis. For example, in 1996 the Food and Drug Administration of America required that the label included in Dovonex (calcipotriene)—a product containing 0.005% calcipotriol—be amended to indicate that approximately 25% of patients experienced skin irritation, and approximately 10% worsening of psoriasis. In addition, it has been reported that some patients treated with Dovonex have developed hypercalcaemia (see, for example, Hardman K A, Heath D A, Nelson H M Hypercalcaemia associated with calcipotriol (Dovonex) treatment. BMJ. 1993 Apr. 3; 306 (6882):896-896).

Further, it is known in the prior art to treat a number of skin conditions by applying a combination of two or more pharmacologically active compounds. For example, in the treatment of psoriasis, it is possible to use a combination treatment involving a vitamin D analogue, such as calcipotriol, and a corticosteroid, where each of the active compounds is formulated in a separate preparation (for example in U.S. Pat. No. 6,753,013).

Topical pharmaceutical compositions comprising a combination of a vitamin D analogue and a topical corticosteroid are challenging to manufacture. This is because these compounds are stable at different pH values.

For example, the calcipotriol requires a pH value above 8 for maximum stability, whereas corticosteroids, such as betamethasone (9-fluoro-11,17,21-trihydroxy-16-methyl-pregna-1,4-diene-3,20-dione), require pH values in the range 4 to 6 for maximum stability. It is therefore difficult to combine the two active components in a single formulation while maintaining good stability of the active compounds if water is present in the formulation.

U.S. Pat. No. 6,753,013 discloses a pharmaceutical composition for dermal use, which contains at least one vitamin D or vitamin D analogue, at least one corticosteroid and a solvent selected to enable the two active components to coexist without significant degradation, despite their different stability profiles. The compositions, however, are wax-based and include wax or similar excipients, such as soft white paraffin and paraffin liquid. A disadvantage of this composition is that, in order to mix the vitamin D or vitamin D analogue and the corticosteroid into the wax, the wax must be heated to a temperature of 70° C. Such elevated temperatures may damage the drugs in the composition. Furthermore, wax based compositions tend to be rather oily, which after application leave a greasy film on the skin. This is undesirable and can lead to patient non-compliance.

A further disadvantage of the compositions of U.S. Pat. No. 6,753,013 is that in order for the compositions to provide beneficial results in topical treatment, high levels of vitamin D or vitamin D analogue are required in order for sufficient vitamin D or vitamin D analogue to permeate the skin. This is because the compositions exhibit poor diffusion through skin. This is disadvantageous as vitamin D and vitamin D analogues are known skin irritants.

There is a need to formulate an improved composition suitable for topical application which addresses at least some of the problems of the prior art.

SUMMARY OF THE INVENTION

The present inventors have now developed a new composition comprising at least one vitamin D or vitamin D analogue and at least one corticosteroid. The present inventors have surprisingly found that such compositions have an enhanced dermal diffusion rate and/or improved stability compared to known compositions. Such compositions also have an appropriate viscosity such that they are useful for topical application.

Accordingly, the present invention provides a composition suitable for topical application comprising a continuous phase and at least one discontinuous phase, said composition comprising at least one polyaphron dispersion, at least one vitamin D or vitamin D analogue and at least one corticosteroid.

According to another aspect of the present invention there is provided a composition as described herein for use in the treatment of psoriasis.

According to another aspect of the present invention there is provided a composition as described herein for use in the manufacture of a medicament for the treatment of psoriasis.

According to a further aspect of the present invention there is provided a composition as described herein for use in a method of treatment of the human or animal body by therapy.

According to a further aspect there is provided a method of treatment or prophylaxis of psoriasis in a subject which comprises topically applying to a subject an effective amount of a composition as herein described.

In the following description, the meaning of the terms used are as follows: by hydrophilic phase or solvent is meant a liquid phase comprising water, comprising water together with other water-miscible liquids, or comprising a non-aqueous liquid which is miscible with water. By hydrophobic phase or solvent is meant a phase comprising pharmaceutically acceptable liquids such as oils that are immiscible or substantially immiscible with the hydrophilic phase. By immiscible liquids is meant that when mixed together, they separate to form two distinctly separate liquid phases sharing a well-defined interface. By substantially immiscible is meant that two liquids mixed as above having a well defined interface between two phases where each phase may nevertheless contain small quantities of dissolved molecules of the other phase.

According to another aspect of the present invention there is provided a method of making the composition as described herein comprising the following steps:
(i) providing a hydrophilic solvent, optionally comprising at least one vitamin D or vitamin D analogue, and/or at least one corticosteroid, and/or a surfactant;
(ii) providing a hydrophobic solvent optionally comprising at least one vitamin D or vitamin D analogue, and/or at least one corticosteroid, and/or a surfactant;
(iii) mixing the hydrophilic solvent with the hydrophobic solvent under suitable conditions to form the composition comprising at least one polyaphron dispersion, at least one vitamin D or vitamin D analogue and at least one corticosteroid.

According to a further aspect of the present invention there is provided a method of making the composition as described herein comprising the following steps:
preparing a first polyaphron dispersion comprising a vitamin D or vitamin D analogue;
preparing a second polyaphron dispersion comprising a corticosteroid;
and mixing together said first and second polyaphron dispersions to form the composition.

Advantageously, the compositions of the present invention have an enhanced dermal permeation of the active agent compared to known compositions, such as those disclosed in U.S. Pat. No. 6,753,013. Thus, lower levels of active agents may be required in the compositions of the present invention in order to achieve beneficial treatment results. As a result of having lower levels of vitamin D and/or vitamin D analogues in the compositions of the present invention the likelihood of causing skin irritation and/or other side-effects is reduced. This may have the effect of increasing patient compliance with the dosage regime. Advantageously, in the compositions of the present invention the vitamin D and/or vitamin D analogue and the corticosteroid can co-exist in an aqueous composition, having the appropriate and controllable viscosity due to the presence of polyaphron dispersions together with any gelling agents included in the composition. A further particular advantage is that the compositions have good long term stability even at elevated temperature (40° C.). Furthermore, the presence of water in the compositions may be useful for dissolving water-soluble additives such as water-soluble preservatives, antioxidants, water-soluble permeation enhancers and the like.

A further advantage is that compositions of the present invention are typically manufactured at room temperature without the need to apply heat, making it less likely that actives will be damaged in the composition.

A further advantage of the present composition is that it feels less greasy in use compared to, for example, the compositions of U.S. Pat. No. 6,753,013, making it more pleasant to apply and thereby increasing the likelihood of proper patient compliance.

Advantageously the composition of the present invention has low antrophogenic potential (i.e. preferably use of this compound when applied to the skin causes less skin thinning compared to prior art compositions).

A yet further advantage of the composition of the present invention is that it need not comprise a high level of surfactant. In high concentrations surfactants are known to cause skin irritation. It is therefore desirable to keep the surfactant level to a minimum when applied to skin, and in particular to damaged skin such as in the case of psoriasis. Preferably the compositions of the present invention comprise less than 4% by weight of surfactant, more preferably less than 3%, more preferably still less than 2% by weight of the total composition.

By polyaphron dispersion as used herein is meant a particular kind of hydrophilic liquid-in-hydrophobic liquid or hydrophobic liquid-in-hydrophilic liquid dispersion comprising (a) a hydrophilic liquid miscible phase, (b) a second hydrophobic phase being immiscible or substantially immiscible with the first phase and (c) one or more surfactants, wherein the dispersed or discontinuous phase is in the form of small (e.g. micron to sub-micron diameter, but more usually at least 1 micron diameter) droplets, and the whole having the following characteristics, which distinguish polyaphron dispersions from conventional or common emulsions and other dispersion types:

1. They are capable of existing in a stable form wherein the volume fraction of the dispersed phase ($\phi_{ip}$) is greater than 0.7 and can be as high as 0.97. ($\phi_{ip}$ is the volume ratio of discontinuous to continuous phase expressed as a fraction).
2. The microscopic appearance of polyaphron dispersions where $\phi_{ip}$ is greater than 0.7 is that of an aggregate of individual droplets, pushed closely together into polyhedral shapes, resembling the appearance of a gas foam. In this form, the dispersion has gel-like properties and is referred to as a Gel Polyaphron Dispersion (GPD).
3. Stable polyaphron dispersions can be formed with a surfactant concentration less than 3% and more typically less than 2% by weight of the total composition.
4. Gel Polyaphron Dispersions (as described in 2 above) can be diluted to any extent by the addition of more continuous phase without the addition of more surfactant, when the gel-like properties disappear. Once $\phi_{ip}$ has been reduced to below 0.7, the individual droplets of internal phase become separated to take the form of spherical droplets, which remain stable and intact but which may nevertheless join together in loose associations and float to the top or sink to the bottom of the diluted dispersion (depending on the relative densities of the two phases). In this diluted form each droplet is referred to as a Colloidal Liquid Aphron (CLA). Simple shaking of the diluted dispersion instantly causes a homogeneous, stable dispersion of Colloidal Liquid Aphrons to re-form.

Each of the above characteristics and a combination of them clearly differentiate the polyaphron dispersions of the present invention from conventional emulsions and other dispersion types which do not have all of those characteristics. Polyaphron dispersions are disclosed in the following literature references by Sebba: "Biliquid Foams", J. Colloid and Interface Science, 40 (1972) 468-474 and "The Behaviour of Minute Oil Droplets Encapsulated in a Water Film", Colloid Polymer Sciences, 257 (1979) 392-396, Hicks "Investigating the Generation, Characterisation, and Structure of Biliquid Foams", PhD Thesis, University of Bristol, 2005, Crutchley "The Encapsulation of Oils and Oil Soluble Substances Within Polymer Films", PhD Thesis, The University of Leeds, 2006 and Lye and Stuckey, Colloid and Surfaces, 131 (1998) 119-136. Aphrons are also disclosed in U.S. Pat. No. 4,486,333 and WO 97/32559.

Polyaphron dispersions are sometimes referred to as 'Biliquid Foams', 'High Internal Phase Emulsions (HIPEs)', 'High Internal Phase Ratio Emulsions (HIPREs)' and 'Gel Emulsions'. In U.S. Pat. No. 5,573,757 a composition comprising a polyaphron dispersion is described as "a viscoelastic gel". All descriptions that refer to dispersions having the characteristics described above are polyaphron dispersions as used in the present invention.

By "topical application" is meant application to human or animal, preferably to the skin, including for example the face, scalp, feet, limbs or trunk.

The present invention will now be further described. In the following passages different aspects of the invention are defined in more detail. Each aspect so defined may be combined with any other aspect or aspects unless clearly indicated to the contrary. In particular any feature indicated as being preferred or advantageous may be combined with any other feature or features indicated as being preferred or advantageous.

As described above polyaphron dispersions comprise a continuous phase, a discontinuous phase and a surfactant. The discontinuous phase is preferably a substantially hydrophobic internal phase, commonly known as an oil internal phase. Preferably, the discontinuous phase comprises a pharmaceutically acceptable oil phase.

Examples of oils which may be used in the present invention include almond oil, babassu oil, blackcurrant seed oil, borage oil, canola oil, castor oil, coconut oil, cod liver oil, corn oil, cottonseed oil, evening primrose oil, fish oil, grapeseed oil, mustard seed oil, oat oil, olive oil, palm kernel oil, palm oil, peanut oil, rapeseed oil, safflower oil, sesame oil, shark liver oil, squalane, soybean oil, sunflower oil, walnut oil, wheat germ oil, hydrogenated castor oil, hydrogenated coconut oil, hydrogenated cottonseed oil, hydrogenated palm oil, hydrogenated soybean oil, partially hydrogenated soybean oil, hydrogenated vegetable oil, isopropyl myristate, isopropyl isostearate, isopropyl palmitate, modified triglycerides, caprylic/capric glycerides, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/caprate/stearate, glyceryl trilaurate, glyceryl trilinoleate, glyceryl trilinolenate, glyceryl trioleate, glyceryl triundecanoate, linoleic glycerides, saturated polyglycolized glycerides, synthetic medium chain triglyceride containing primarily $C_8$-$C_{12}$ fatty acid chains, medium chain triglycerides, long chain triglycerides, modified triglycerides, fractionated triglycerides, and mixtures thereof.

Suitably the discontinuous phase comprises monoglycerides, diglycerides, or triglycerides.

It will be understood that other suitable oils may be used in the present invention.

In a preferred embodiment, the discontinuous phase comprises or is caprylic/capric triglyceride and/or isopropyl myristate (IPM).

The discontinuous phase may, for example, confer an emollient, occlusive, moisturising, conditioning or other cosmetic or pharmaceutical benefit to the skin. It may also increase the viscosity of the composition and may confer solvency to the active or actives. It may contain materials providing a heating or cooling effect when applied to the skin (for example capsaicum or menthol).

The composition may comprise at least 1% by weight of the discontinuous phase, more preferably at least 10% by weight, at least 25%, at least 50%, at least 80% by weight of the discontinuous phase based on the weight of the total composition.

The compositions of the present invention may be non-aqueous, substantially non-aqueous or aqueous.

By the term "non-aqueous composition" as used herein is meant a composition which is effectively free of water and does not contain water that has been deliberately added. A "non-aqueous composition" as used herein preferably has less than 0.5% by weight of water based on the total weight of the composition, more preferably less than 0.2% by weight of water, most preferably less than 0.1% by weight of water based on the total weight of the composition.

By the term "substantially non-aqueous" as used herein is meant a composition comprising less than 5% by weight, more preferably less than 4.5% by weight, of water based on the total weight of the composition.

By the term "aqueous composition" is meant a composition comprising at least 5% by weight of water based on the total weight of the composition. Preferably, the aqueous composition comprises at least 10%, or at least 15% by weight of water based on the total weight of the composition. The aqueous composition may comprises at least 35%, or at least 40% by weight based on the total weight of the composition. For aqueous compositions, preferably the percentage of water is from 5% to 90% by weight, and more preferably from 5% to 50% by weight and most preferably from 8% to 20% by weight based on the total weight of the composition.

In one embodiment of the present invention there is provided an aqueous composition suitable for topical application comprising a continuous phase and at least one discontinuous phase, said composition comprising at least one polyaphron dispersion, at least one vitamin D or vitamin D analogue and at least one corticosteroid. In this embodiment preferably the composition comprises at least 5%, more preferably at least 6%, more preferably still at least 8% by weight of water based on the total weight of the composition.

Preferably, the aqueous composition suitable for topical application comprises from 60 to 95% by weight of discontinuous phase, and from 5 to 40% by weight of continuous phase based on the total weight of the composition, wherein preferably the composition comprises from 5 to 40%, or from 5 to 30%, or from 8 to 20% by weight of water based on the total weight of the composition, wherein discontinuous phase and/or the continuous phase comprise at least one the vitamin D or vitamin D analogue and at least one corticosteroid and at least one surfactant. More preferably the aqueous composition suitable for topical application comprises from 70 to 90% by weight of discontinuous phase, and from 10 to 30% weight of continuous phase based on the total weight of the composition, wherein preferably the composition comprises at least from 5 to 30%, or from 8 to 20% by weight of water based on the total weight of the composition, wherein discontinuous phase and/or the continuous phase comprise at least one the vitamin D or vitamin D analogue and at least one corticosteroid and at least one surfactant.

Preferably the composition of the present invention is dispersible in water. Preferably the composition of the present invention is dilutable in water. This increases the flexibility of use of the invention, for example in improving the application of the composition to the scalp through hair by leaving the hair wet, or from rinsing the preparation from any topical surface should the desire or need arise, or by the easy removal by rinsing of product from accidental contamination of clothing. These advantages improve the in-use experience of users and improve patient compliance.

The advantages of providing an aqueous composition comprising at least one vitamin D or vitamin D analogue and at least one corticosteroid include improved drug permeation, control of drug permeation by the inclusion of certain permeation enhancers and permeation retarders and improved skin feel.

When the continuous or external phase of the composition comprises water, close control of the pH within suitable limits is desired. Such control is desirable in order to obtain a stable composition. The present inventors have found that stable compositions of the present invention may be obtained when the pH of the composition is adjusted to a pH of from 7.0 to 8.5, more preferably still to a pH of from 7.25 to 7.75. It will be understood that any suitable acid or base may be used to adjust the pH to the appropriate value or pH range: Typically the pH of the composition will need to be raised by the addition of a base, which suitably may be triethanolamine. Other suitable bases include, but are not limited to trishydroxymethylaminomethane (tris) and sodium hydroxide. Advantageously and preferably, the pH of the composition may be stabilized by the incorporation of a suitable buffer into the aqueous phase. Suitable buffer systems having a pH within the specified range will be familiar to those skilled in the art.

The continuous phase may comprise or consist essentially of a pharmaceutically acceptable liquid that is miscible or substantially miscible with water, preferably a compound of formula $R_1$—OH where $R_1$ is $C_1$-$C_{10}$ alkyl and/or a compound of formula HO—$R_2$—H where $R_2$ is —$(C_2H_4)_n$ or —$(C_3H_6)_n$ where n is 1 to 100, preferably 1 to 25. $R_1$ and $R_2$ may be linear or branched. Preferably $R_1$ is $C_1$-$C_4$ alkyl. n is preferably 1 to 25. Preferably the continuous phase comprises propylene glycol, polyethylene glycol, glyercol, ethanol, isopropyl alcohol, or a mixture thereof. Where the continuous phase comprises polyethylene glycol or polypropylene glycol, the polyethylene or polypropylene glycol is preferably a polyethylene glycol which is liquid at room temperature (20° C.). The polyethylene glycol may, for example, contain from 1 to 12 ethylene or propylene oxide units and/or have a molecular weight of up to 600.

In one embodiment of the present invention the composition, and preferably the polyaphron dispersion, comprises from 0 to 60 wt %, preferably from 0 to 20 wt %, more preferably from 0 to 15 wt %, of a $C_1$-$C_4$ alcohol, ethylene glycol, a liquid polyethylene glycol, propylene glycol, a liquid polypropylene glycol, diethylene glycol mono ethyl ether or mixtures thereof. One of the advantages of the composition of the present invention over prior art compositions is that high levels of alcohol are not needed as skin permeation enhancers. Alcohol is known to cause skin irritation when applied to damaged skin. The compositions of the present invention have the advantage that enhanced permeation can be achieved even without the need for alcohol to be present, or without the need for high levels of alcohol. The present inventors have surprisingly found that it is advantageous for the composition of the present invention to comprise from 0 to 25% by weight of alcohol, more preferably from 0 to 15% by weight based on the total weight of the composition. Preferably the alcohol is isopropanol and/or propylene glycol. Such compositions have improved drug delivery properties.

It will be understood that other suitable hydrophilic solvents may be used in the continuous phase of the polyaphrons.

The surfactant used in the present invention may be incorporated into either or both phases of the polyaphron dispersion. Suitable surfactants include an alkyl polyglycol ether, an alkyl polyglycol ester, an ethoxylated alcohol, a polyoxyethylene sorbitan fatty acid ester, a polyoxyethylene fatty acid ester, an ionic or non-ionic surfactant, a hydrogenated castor oil/polyoxyethylene glycol adduct containing from 25 to 60 ethoxy groups a castor oil/polyoxyethylene glycol adduct containing from 25 to 45 ethoxy groups, a sorbitan fatty acid ester (for example Span 20 or Span 80), a block copolymer of ethylene oxide and propylene oxide (for example Pluronic L121 or Pluronic F68), or a mixture thereof.

It will be understood that other suitable surfactants may be used.

Preferably the compositions of the present invention comprise less than 4% by weight of surfactant, more preferably less than 3%, more preferably still less than 2% by weight of the total composition.

The composition of the present invention may comprise at least one vitamin D or vitamin D analogue predominantly in the continuous phase, or predominantly in the discontinuous phase. Most preferably at least one vitamin D or vitamin D analogue is present predominantly in the discontinuous phase.

The vitamin D analogue employed in the composition of the present invention may, for example, be calcipotriol, seocalcitol, calcitriol, calcipotriol monohydrate, tacalcitol, maxacalcitol, paricalcitol, falecalcitriol, becocalcidiol, 1α,24S-dihydroxy-vitamin D2, 1(S),3(R)-dihydroxy-20(R)-[((3-(2-hydroxy-2-propyl)-phenyl)-methoxy)-methyl]-9,10-seco-pregna-5(Z),7(E),10(19)-triene, or a mixture thereof. More preferably, the vitamin D anolgue is calcipotriol, calcitriol, tacalcitol, maxacalcitol, 1α,24S-dihydroxy-vitamin D2, 1(S),3(R)-dihydroxy-20(R)-[((3-(2-hydroxy-2-propyl)-phenyl)-methoxy)-methyl]-9,10-seco-pregna-5(Z),7(E),10(19)-triene, or a mixture thereof. Most preferably, the vitamin D analogues are calcipotriol and calcipotriol monohydrate. Other examples of suitable vitamin D analogues are described in U.S. Pat. No. 6,753,013.

Synthetic vitamin D analogues are preferred in the compositions of the present invention over naturally occurring vitamin D or vitamin D derivatives, since the therapeutic effects of the latter may be less selective for the treatment of skin diseases, such as psoriasis.

The composition of the present invention may comprise from 0.0001 to 0.05% by weight of vitamin D or vitamin D analogue, preferably from 0.001 to 0.01% by weight and more preferably from 0.0025 to 0.005% by weight of the total composition.

The corticosteroid may be predominantly in the continuous phase, or predominantly in the discontinuous phase. Preferably, the corticosteroid is predominantly in the discontinuous phase. More preferably, both the corticosteroid and the vitamin D or a vitamin D analogue are predominantly in the discontinuous phase. The range of weight ratios of corticosteroid to vitamin D or vitamin D analogue is preferably 4:1 to 50:1 and more preferably 8:1 to 20:1 and most preferably 9:1 to 11:1.

Preferably, the corticosteroid is selected from one or more of Betamethasone (9α-fluoro-11β,17α,21-trihydroxy-16β-methylpregna-1,4-diene-3,20-dione) or esters thereof such as the 21-acetate, 17-adamantoate, 17-benzoate, 17-valerate, and 17,21-dipropionate; Alclomethasone or esters thereof such as the 17,21-dipropionate; Clobetasole or esters thereof such as the propionate; Clobetasone or esters thereof such as the 17-butyrate; Desoximetasone; Diflucortolon or esters thereof, Diaflorasone or esters thereof such as the 17,21-diacetate; Fluocinonid; Flumetasone or esters thereof such as the 21-pivalate; Fluocinolone or ethers thereof such as the acetonide; Fluticasone or ester thereof such as the 17-propionate; Fluprednidene or esters thereof such as the 21-acetate; Halcinonide; Hydrocortisone or esters thereof such as the 17-butyrate; Mometasone or esters thereof such as the 17-(2-furoate); and Triamcinolon or ethers or esters thereof such as the acetonide. Nitric oxide donating corticosteroids may also be selected, such as TPI 1020 (NicOx). More preferably the corticosteroid is selected from one or more of Betamethasone or esters thereof such as the 17-valerate or the 17,21-dipropionate; Clobetasole or esters thereof such as the propionate; Triamcinolon or ethers or esters thereof such as the acetonide or the acetonide-21-N-benzoyl-2-methyl-8-alaninate or the acetonide-21-(3,3-dimethylbutyrate); or Hydrocortisone or esters thereof such as the 17-butyrate. Most preferably, the corticosteroid is betamethasone 17,21-dipropionate.

The composition of the present invention preferably comprises from 0.001 to 1.0% by weight of corticosteroid, more preferably from 0.01% to 0.075% by weight and more preferably still from 0.025 to 0.05% by weight of the total composition.

The composition of the present invention may further comprise a gelling agent and/or a rheology modifying agent, such as a viscosity modifier.

The gelling agent may, for example, be selected from alginate gums or their salts, guar gum, locust bean gum, xanthan gum, gum acacia, gelatin, hydroxymethyl-cellulose hydroxyethylcellulose, hydroxypropyl-cellulose, carboxymethylcellulose or its salts, bentonites, magnesium aluminium silicates, "Carbomers" (salts of cross-linked polymers of acrylic acid), or glyceryl polymethacrylates or their dispersions in glycols. It will be understood that other suitable gelling agents may be used. Additionally, the inventors have discovered that some of the gelling agents (for example, carbomers) may also function as a chemical buffering agents thus preventing unwanted variation in the pH of the composition during storage and use.

Preferably, the composition of the present invention comprises from 0.05 to 5.0% by weight of a gelling agent, preferably from 0.1 to 2.0% by weight and more preferably from 0.2 to 1.0% by weight of the total composition.

In one embodiment of the present invention the composition is in the form of a gel. The gel may be formed from one, two, three or more polyahron dispersions. Preferably, the composition is an aqueous gel. As used herein the term aqueous gel means that the gel comprises at least 5% of water based on the total weight of the gel. Preferably, the gel comprises at least 10%, at least 15%, at least 35% or at least 40% by weight of water based on the total weight of the gel.

The composition of the present invention may be used in a method of treatment of the human or animal body by therapy. Further, the composition of the present invention may be used in the treatment of psoriasis. Also the composition of the present invention may be used in the manufacture of a medicament for treatment of psoriasis.

In one embodiment of the present invention, the composition as described herein may be applied to the scalp or other skin surface through hair. Preferably in this embodiment the hair is wetted (for example by use of water with or without shampoo, and then towel dried). The product may then be applied to the scalp in a suitable amount and then massaged into the scalp through the hair. The hair may then be left to dry naturally or dried using a hair dryer. Advantageously, the water-dispersible form of the formulation enables an even distribution of the actives on the skin using this process. Alternatively, or additionally, the composition may be massaged into the scalp through dry hair and left for a suitable period (which may be 8 to 12 hours) after which the excess or reminder may be rinsed out with water with or without shampoo. Preferably the composition is applied to an animal in unit dosage form.

The compositions of the present invention may also contain other additives such as preservatives (for instance to prevent microbiological spoilage), buffering agents (for the control of pH and to avoid instability and damage to the skin's acid mantle), antioxidants and permeation enhancers. These additives may be included in the continuous or the discontinuous phase of the polyaphron dispersion.

It will be understood that the inclusion of these additives will be at the levels and with the type of materials which are found to be effective and useful. Care needs to be taken in the choice and amount of these additives to prevent compromise to the other performance advantages of the present invention.

In one embodiment of the present invention, the vitamin D or vitamin D analogue of the present invention is dispersed and/or dissolved in the discontinuous phase of a first polyaphron dispersion. The corticosteroid is dispersed and/or dissolved in the discontinuous phase of a second polyaphron dispersion. The first and the second polyaphron dispersions are then mixed together to form the composition of the present invention. Optionally, a third or further polyaphron dispersion may also be present in the composition of the present invention. The third or further polyaphron dispersion may, for example, comprise agents such as emollient oils (to improve in use 'feel'), occlusive oils to prevent skin dehydration and to enhance skin permeation by the actives, agents that provide a heating or cooling sensation when applied to the skin or sunscreens. Preferably these agents will be present in the discontinuous phase of the polyaphron dispersions.

In one embodiment of the present invention, the vitamin D analogue is calcipotriol or calcipotriol monohydrate.

In a particularly preferred composition the discontinuous phase is a caprylic/capric triglyceride, the continuous phase is demineralised water, the vitamin D analogue is calcipotriol and the corticosteroid is betamethasone dipropionate.

In one embodiment of the present invention, the composition comprises at least one discontinuous phase which comprises at least one of capric/caprylic triglycerides, squalane, dimethicone, cyclomethicone and mixtures of two or more thereof, the vitamin D analogue is calcipotriol and the corticosteroid is betamethasone dipropionate. Preferred surfactants in this embodiment are Laureth-4 and Poloxamer 188. Preferably the continuous phase comprises water. Such an embodiment is exemplified by Example 1. Advantageously such a composition is stable over an extended period of time, for example over 3 months, 6 months or 9 months. This composition provides good solubility for the actives, has an enhanced permeation and has a very pleasant feel on the skin during and after application.

In a further embodiment, the composition of the present invention comprises at least one discontinuous phase which comprises at least one of capric/caprylic triglycerides, squalane, dimethicone, isopropyl myristate, cyclomethicone and mixtures of two or more thereof, the vitamin D analogue is calcipotriol and the corticosteroid is betamethasone dipropionate, preferred surfactants in this embodiment are Laureth-4 and Poloxamer 188. Preferably the continuous phase comprises water and polyacrylic acid which is neutralized with triethanolamine, so as to form a gel to control viscosity. Such an embodiment is exemplified by Example 3. Advantageously this composition uses an aqueous gel phase to provide a greater cream-like viscosity and excellent pH buffering capacity.

In a further embodiment, the composition of the present invention comprises at least one discontinuous phase which comprises at least one of capric/caprylic triglycerides, squalane, dimethicone, isopropyl myristate and cyclomethicone and mixtures of two or more thereof, the vitamin D analogue is calcipotriol and the corticosteroid is betamethasone dipropionate, preferred surfactants in this embodiment are Laureth-4 and Poloxamer 188. Preferably the continuous phase comprises water and xanthane gum, so as to form a gel to control viscosity. Such an embodiment is exemplified by Example 5. The inventors have found that the use of xanthane produces excellent stability at a lower viscosity which is of particular use as a lotion rather than a cream.

In a further embodiment, the composition of the present invention comprises at least one discontinuous phase which comprises at least one of capric/caprylic triglycerides, squalane, dimethicone, silicone elastomer, isopropyl myristate and cyclomethicone and mixtures of two or more thereof, the vitamin D analogue is calcipotriol and the corticosteroid is betamethasone dipropionate, preferred surfactants in this embodiment are Laureth-4 and Poloxamer 188. Preferably the continuous phase comprises water, isopropyl alcohol and polyacrylic acid which is neutralized with triethanolamine, so as to form a gel to control viscosity. Such an embodiment is exemplified by Example 13. The silicone elastomer is added to the discontinous phase to improve the cosmetic feel of the product. This embodiment provides still further pleasant 'after-feel' (the residual feel of the skin after application) and increased skin barrier properties.

Accordingly to one aspect of the present invention, there is provided a method of making the composition as described herein comprising the following steps:
  (i) providing a hydrophilic solvent, optionally comprising at least one vitamin D or vitamin D analogue, and/or at least one corticosteroid, and/or a surfactant;
  (ii) providing a hydrophobic solvent optionally comprising at least one vitamin D or vitamin D analogue, and/or at least one corticosteroid, and/or a surfactant;
  (iii) mixing the hydrophilic with the hydrophobic solvent under suitable conditions to form the composition comprising at least one polyaphron dispersion, at least one vitamin D or vitamin D analogue and at least one corticosteroid.

Suitable methods for preparing polyaphron dispersions are described in U.S. Pat. No. 4,486,333. It will be understood by those skilled in the art that other manufacturing methods may be used, as appropriate.

Accordingly to another aspect of the present invention, there is provided a method of making the composition as described herein comprising the following steps:
  preparing a first polyaphron dispersion comprising a vitamin D or vitamin D analogue;
  preparing a second polyaphron dispersion comprising a corticosteroid;
  and mixing together said first and second polyaphron dispersions to form the composition.

The method may further comprise:
  preparing a third or further polyaphron dispersion comprising an active agent, such as one or more of a sunscreening agent, a cooling agent, a warming agent, an antipuritic agent, an aesthetic agent, a cosmetic masking agent, a foaming agent, a fragrance, a colouring agent, an antioxidant or an emollient oil and including mixtures thereof;
  and mixing said third or further polyaphron with said first and second polyaphron dispersions to form the composition.

The composition as described herein may be delivered to the skin in the form of an aerosol or a spray. For example EP 1,575,542 teaches the incorporation of a biliquid foam into aerosols.

The composition of the present invention may be incorporated into aerosols by the addition of water and propellant gas (for example butane).

The composition of the present invention may be in the form of, for example, a lotion or a cream. The composition may be stored in any suitable jar, tube, bottle, sachet, aerosol, spray applicator or pump action sealed container. Advantageously in order for the compositions to remain stable the containers preferably prevent oxygen from entering the container. Preferably the compositions of the present invention are sealed in air tight containers in order to prevent degradation of the compositions prior to use.

The present invention will now be described further, by way of example only, with reference to the following figures, in which:

FIG. 1 is a HPLC chromatogram of a stable sample (Example 7). Peaks for calcipotriol (3.9 min) and betamethasone diproprionate (BDP) (5.3 min). No evidence of degradation products is observed. HPLC conditions are:
  Column: NovaPakC18, 4μ particle size, 3.9×150 mm column (Waters), Mobile phase: 55% acetronitrile in water. Flow rate: 1 ml/minute. Column Temperature: 25° C.

Figure 2:
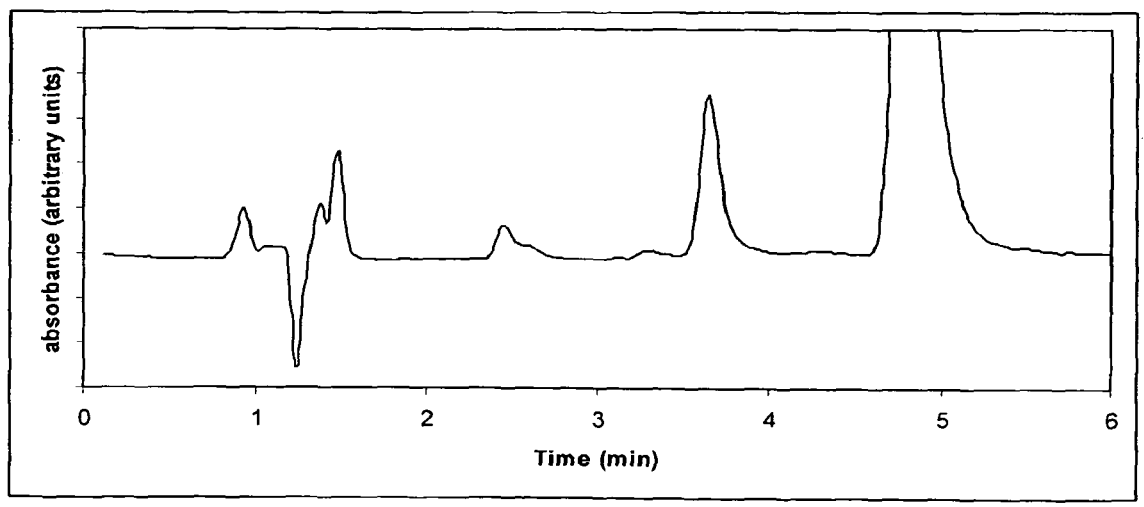

FIG. 2 is a HPLC chromatogram of an unstable sample. Degradation of betamethasone diproprionate is observed (extra peak and shoulder at 2.5 minutes) and there is some evidence of calcipotriol degradation (very minor peak at 3.3 min). HPLC conditions are: Column: NovaPakC18, 4μ particle size, 3.9×150 mm column (Waters), Mobile phase: 55% acetronitrile in water. Flow rate: 1 ml/minute. Column Temperature: 25° C.

Figure 3:
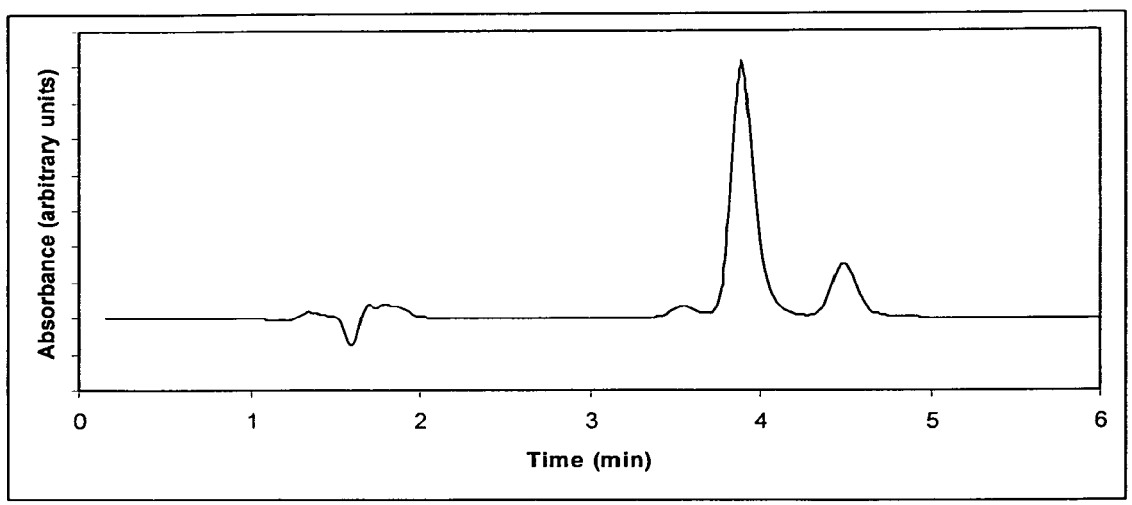

FIG. 3 is a HPLC chromatogram of the degradation of calcipotriol as evidenced by the presence of extraneous peaks (4.5 min and 3.6 min) either side of the main calcipotriol peak (3.9 min). No betamethasone diproprionate (BDP) was present in this sample, thus these peaks cannot be due to BDP degradation. HPLC conditions are:

Column: NovaPakC18, 4µ particle size, 3.9×150 mm column (Waters), Mobile phase: 55% acetonitrile in water. Flow rate: 1 ml/minute. Column Temperature: 25° C.

DEFINITION OF STABILITY

For the present invention, a product is considered to be storage stable if it meets with the following criteria.

The product is stored in closed, airtight glass containers with headspace comprising no more than 5% by volume of the total usable volume of the container.

The product and the container as defined above are stored at a constant temperature of 40° C. in a standard laboratory oven (for example, Heraeus 'Function Line' air circulating oven model UT6, temperature control±0.3° C. at 150° C.).

The product is examined at the end of the examination period. The examination period is at least 3 months and preferably at least 6 months from the start date of storage.

The pass criteria are as follows:

| Procedure | Pass Criteria |
| --- | --- |
| Visual comparison of the appearance of the stored sample compared to a standard sample stored at 20° C. for the same period. | Visual assessment indicates very little, if any, difference between stored sample and standard. In particular, appearance of the sample is uniform throughout with no sign of separation into two or more distinct phases. |
| A microscopic examination at a magnification of at least 200X comparing the microscopic appearance of the stored sample with a stored image of its appearance at the date of commencement of storage | Examination indicates very little, if any change in the size and size distribution of polyaphron droplets, with no sign of separated phases. |
| Analysis of the pharmacologically active components of the formulation by the extraction and HPLC method given hereinunder | Each active shall not have diminished by more than 5% by weight of the original content at the date of commencement of the storage test after 3 months of storage. Known decomposition products of the actives, if any such are present, collectively constitute no more than 5% of the original active based upon area under the curve measurements. See FIGS. 1-3 for further clarification. |

Any stored samples that meet the above criteria under the test conditions given above are considered to be storage stable for the purposes of this invention.

The FDA's 'Guidance for Industry Q1A (R2) Stability Testing of New Drug Substance and Products' although non-binding, specifies accelerated storage conditions that include storage at specific temperatures (e.g. 40° C.) for a specific time (6 months) and at a controlled relative humidity (75% RH). The European Agency for the Evaluation of Medicinal Products, ICH Q1A (R2) 'Stability Testing Guidelines: Stability Testing of New Drug Substances and Products' specifies identical conditions for accelerated storage testing. The stability test method specified above for the purpose of this invention does not include provision for the control of relative humidity since storage takes place in closed glass containers whose walls and closures are impervious to the passage of water vapour.

The above definition of storage stable is definitive for the purposes of this invention. However, storage data on some examples were obtained by substituting close-sealed eppendorf tubes for closed glass containers (glass). This method was adopted to cope with relatively small amounts of sample and gives a reasonable approximation to the definitive method. The examination procedure for eppendorf tubes (plastic) is identical to that of the definitive method.

The following Examples further illustrate the present invention.

Example 1

Three gel polyaphron dispersions of the following compositions were prepared by the following method.

| Gel POLYAPHRON DISPERSION 1 | |
| --- | --- |
| | % |
| Oil Phase | |
| Calcipotriol solution* (0.0695%) in Caprylic/Capric Triglyceride (Mygliol 812 - Condea) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 2 | |
| --- | --- |
| | % |
| Oil Phase | |
| Betamethasone Dipropionate solution** (0.3465%) in Caprylic/Capric Triglyceride (Mygliol 812 - Condea) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 3 | |
| --- | --- |
| | % w/w |
| Oil Phase | |
| Squalane (Olive-derived - A & E Connock) | 9.00 |
| Dimethicone (Q7-1920, 100 CP - Dow Corning) | 44.10 |
| Cyclomethicone (STb5NF - Dow Corning) | 36.00 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| FINAL PRODUCT | % w/w |
| --- | --- |
| GEL POLYAPHRON DISPERSION 1 | 7.20 |
| GEL POLYAPHRON DISPERSION 2 | 18.60 |
| GEL POLYAPHRON DISPERSION 3 | 74.20 |

*The Calcipotriol content in the final formulation is 50 µg/g.

**The betamethasone dipropionate content in the final formulation is 643 µg/g (equivalent to 500 µg/g of betamethasone).

Manufacturing Method

Three polyaphron dispersions were made individually by the following method:

A low form, 250 ml laboratory beaker (internal diameter 6.5 cm) was charged with sufficient aqueous (continuous) phase to make 30 g of gel polyaphron. This was stirred at 200 rpm with a four-bladed impeller having a diameter of 6.0 cm whilst adding the oil (discontinuous) phase drop wise from a Pasteur pipette. The rate of addition at the start of the process was slow (approximately one drop every 7 seconds) but was speeded up once 10% of the oil phase had been added so that the total time to make the gel polyaphron was approximately 20 minutes.

Prior to the manufacture of each gel polyaphron dispersion, any active was dissolved in the appropriate phase by gentle stirring overnight with a magnetic stirrer at room temperature in a covered beaker.

To form the final product, the three individual polyaphron dispersions were mixed together.

Stability Measurements—Conditions 1a

Stability measurements made using the method outlined below. In this example the storage data was obtained in an eppendorf tube.

The calcipotriol and betamethasone were extracted from the composition of Example 1 into isopropanol and assayed by HPLC under the conditions given below.

Hplc Conditions:

Column: NovaPakC18, 4µ particle size, 3.9×150 mm column (Waters)

Mobile phase: 47% acetonitrile in water.

Flow rate: 1 ml/minute.

Column Temperature: 25° C.

Retention time for calcipotriol was 6.8 minutes

Retention time for betamethasone was 9.9 minutes.

The inventors observed that after 2 months storage at 40° C., the levels of calcipotriol and betamethasone were 102%±3% and 99%±1% of the original levels, respectively.

Stability Measurements—Conditions 1b

Stability measurements made using the method outlined below. Samples were stored in (airtight) glass jars in a suitable oven maintained at 40° C., as described above.

The calcipotriol and betamethasone were extracted from the composition of Example 1 into isopropanol by mixing the sample in isopropanol followed by sonication and centrifugation. Aliquots of the supernatant were assayed by HPLC under the conditions given below.

Hplc Conditions:

Column: NovaPakC18, 4µ particle size, 3.9×150 mm column (Waters)

Mobile phase: 55% acetonitrile in water.

Flow rate: 1 ml/minute.

Column Temperature: 25° C.

Retention time for calcipotriol was 3.9 minutes Retention time for betamethasone was 5.3 minutes.

The inventors observed that after 2 months storage at 40° C., the levels of calcipotriol and betamethasone were 102%±3% and 99%±1% of the original levels, respectively.

Example 2

| Gel POLYAPHRON DISPERSION 1 | % |
|---|---|
| Oil Phase | |
| Calcipotriol solution* (0.06766%) in Caprylic/Capric Triglyceride (Mygliol 812 - Condea) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 2 | % |
|---|---|
| Oil Phase | |
| Betamethasone Dipropionate solution** (0.3066%) in a 3:2 w/w blend of isopropyl myristate (Lexol IPM NF - Inolex):Caprylic/Capric Triglyceride (Mygliol 812 - Condea) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 3 | % w/w |
|---|---|
| Oil Phase | |
| Squalane (Olive-derived - A & E Connock) | 9.00 |
| Dimethicone (Q7-9120, 100 CP - Dow Corning) | 44.10 |
| Cyclomethicone (STb5NF - Dow Corning) | 36.00 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| AQUEOUS GEL | % w/w |
|---|---|
| Polyacrylic acid (Ultrez 10 - Noveon) | 1.00 |
| Triethanolamine (TEA) | to pH 7.50 |
| Demineralised Water | qs to 100% |

| FINAL PRODUCT | % w/w |
|---|---|
| GEL POLYAPHRON DISPERSION 1 | 9.19 |
| GEL POLYAPHRON DISPERSION 2 | 23.61 |
| GEL POLYAPHRON DISPERSION 3 | 47.27 |
| Propylene glycol | 10.05 |
| Aqueous gel | 9.88 |

\* final calcipotriol level 55.4 µg/g

\*\* final BDP level 645 µg/g, equivalent to 502 µg/g

Manufacturing Method

The method used was as described for Example 1 above except that propylene glycol and the neutralised aqueous gel were added to the final mixture of the three gel polyaphron dispersions, 1, 2 and 3 and then mixed in by simple mixing until the product was a homogeneous mixture of the polyaphron dispersions.

By neutralised gel is meant the addition of triethanolamine (a base) to a dispersion of the polyacrylic acid to form a clear gel having a pH value of 7.5±0.2. The process of neutralisation of polyacrylic acid gels is well known to those skilled in the art.

Stability Measurements

Stability was tested as in Example 1b.

The inventors observed that after 3.5 months storage at 40° C. in glass jars the levels of calcipotriol and betamethasone dipropionate were 104±12% and 95±2% of the original levels respectively.

Stability testing is ongoing with this sample.

Reference is made to Simonsen et al, Drug Development and Industrial Pharmacy, 30(10) (2004) 1095-1102, wherein the authors state that the inclusion of propylene glycol to a product containing both calcipotriol and betamethasone causes rapid decomposition of one or other of the actives depending upon pH, although propylene glycol is a very good flux rate enhancer. They concluded that it was not possible to include propylene glycol in their formulated product. This Example demonstrates that the inventors of the present invention have overcome this problem. Example 2, table 2 in U.S. Pat. No. 6,753,013 illustrates the degradation of calcipotriol in a product comprising calcipotriol, betamethasone dipropionate and propylene glycol after storage for 2.5 months at 40° C.

Example 3

Three gel polyaphron dispersions and an aqueous gel of the following compositions were prepared by the following method.

| Gel POLYAPHRON DISPERSION 1 | |
|---|---|
| | % |
| Oil Phase | |
| Calcipotriol solution* (0.0573%) in a 3:2 w/w blend of isopropyl myristate (Lexol IPM NF - Inolex):Caprylic/Capric Triglyceride (Mygliol 812 - Condea) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 2 | |
|---|---|
| | % |
| Oil Phase | |
| Betamethasone Dipropionate solution** (0.3838%) in Caprylic/Capric Triglyceride (Mygliol 812 - Condea) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 3 | |
|---|---|
| | % w/w |
| Oil Phase | |
| Squalane (Olive-derived - A & E Connock) | 9.00 |
| Dimethicone (Q7-9120, 100 CP - Dow Corning) | 44.10 |
| Cyclomethicone (STb5NF - Dow Corning) | 36.00 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| AQUEOUS GEL | |
|---|---|
| | % w/w |
| Polyacrylic acid (Ultrez 10 - Noveon) | 1.00 |
| Triethanolamine (TEA) | to pH 7.50 |
| Demineralised Water | qs to 100% |

| FINAL PRODUCT | % w/w |
|---|---|
| GEL POLYAPHRON DISPERSION 1 | 12.95 |
| GEL POLYAPHRON DISPERSION 2 | 20.18 |
| GEL POLYAPHRON DISPERSION 3 | 57.05 |
| AQUEOUS GEL | 9.82 |

*The Calcipotriol content in the final formulation is 66.1 µg/g.

**The betamethasone dipropionate content in the final formulation is 690 µg/g (equivalent to 537 µg/g of betamethasone).

Manufacturing Method

The method used was as described for Example 1 above except that the neutralised aqueous gel was added to the final mixture of the three gel polyaphron dispersions, 1, 2 and 3 and then mixed in by simple mixing until the product was a homogeneous mixture of the polyaphron dispersions.

Stability Measurements

Stability was tested as in Example 1b

The inventors observed that after 9 months storage at 40° C. in a sealed glass jar the levels of calcipotriol and betamethasone dipropionate were 97±7% and 105±6% of the original levels respectively.

Example 4

Three gel polyaphron dispersions of the following compositions were prepared by the following method.

| Gel POLYAPHRON DISPERSION 1 | |
|---|---|
| | % |
| Oil Phase | |
| Calcipotriol solution* (0.0237%) isopropyl myristate (Lexol IPM NF - Inolex) | 89.10 |
| Laureth-4 (Volpo L4 - Croda) | 0.90 |

-continued

Gel POLYAPHRON DISPERSION 1

| | % |
|---|---|
| Aqueous Phase | |
| Poloxamer 188 (Pluronic F68 - BASF) | 1.00 |
| Sucrose (Fisher) | 1.00 |
| Demineralised Water | 8.00 |

Gel POLYAPHRON DISPERSION 2

| | % |
|---|---|
| Oil Phase | |
| Betamethasone Dipropionate solution** (0.3085%) in isopropyl myristate(Lexol IPM NF - Inolex) | 89.10 |
| Laureth-4 (Volpo L4 - Croda) | 0.90 |
| Aqueous Phase | |
| Poloxamer 188 (Pluronic F68 - BASF) | 1.00 |
| Sucrose (Fisher) | 1.00 |
| Demineralised Water | 8.00 |

Gel POLYAPHRON DISPERSION 3

| | % w/w |
|---|---|
| Oil Phase | |
| Squalane (Olive-derived - A & E Connock) | 20.00 |
| Dimethicone (Q7-9120, 20 CP - Dow Corning) | 35.00 |
| Cyclomethicone (STb5NF - Dow Corning) | 29.10 |
| Elastomer DC10 (Dow Corning) | 5.00 |
| Laureth-4 (Volpo L4 - Croda) | 0.90 |
| Aqueous Phase | |
| Poloxamer 188 (Pluronic F68 - BASF) | 1.00 |
| Sucrose (Fisher) | 1.00 |
| Demineralised Water | 8.00 |

| FINAL PRODUCT | % w/w |
|---|---|
| GEL POLYAPHRON DISPERSION 1 | 27.99 |
| GEL POLYAPHRON DISPERSION 2 | 26.56 |
| GEL POLYAPHRON DISPERSION 3 | 45.45 |

*The Calcipotriol content in the final formulation is 59.0 µg/g.

**The betamethasone dipropionate content in the final formulation is 730 µg/g (equivalent to 568 µg/g of betamethasone).

Manufacturing Method

The method used was as described for Example 1.

Stability Measurements

Stability was tested as in Example 1b

The inventors observed that after 4.5 months storage at 40° C. in a sealed glass jar the levels of calcipotriol and betamethasone dipropionate were 100% and 119% of the original levels respectively.

After 6 months, the levels of calcipotriol and betamethasone dipropionate were 42% and 65% of the original levels respectively.

Stability testing is ongoing with this sample

Example 5

Three gel polyaphron dispersions and an aqueous gel of the following compositions were prepared by the following method.

Gel POLYAPHRON DISPERSION 1

| | % |
|---|---|
| Oil Phase | |
| Calcipotriol solution* (0.0452%) in isopropyl myristate (Lexol IPM NF - Inolex) | 89.10 |
| Polyoxyethylene (20) sorbitan monooleate(Surfacare T80) | 0.90 |
| Aqueous Phase | |
| Poloxamer 188 (Pluronic F68 - BASF) | 1.00 |
| Demineralised Water | 9.00 |

Gel POLYAPHRON DISPERSION 2

| | % |
|---|---|
| Oil Phase | |
| Betamethasone Dipropionate solution** (0.2889%) in isopropyl myristate (Lexol IPM NF - Inolex) | 89.10 |
| Polyoxyethylene (20) sorbitan monooleate(Surfacare T80) | 0.90 |
| Aqueous Phase | |
| Poloxamer 188 (Pluronic F68 - BASF) | 1.00 |
| Demineralised Water | 9.00 |

Gel POLYAPHRON DISPERSION 3

| | % w/w |
|---|---|
| Oil Phase | |
| Squalane (Olive-derived - A & E Connock) | 9.00 |
| Dimethicone (Q7-9120, 100 CP - Dow Corning) | 44.10 |
| Cyclomethicone (STb5NF - Dow Corning) | 36.00 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

AQUEOUS GEL

| | % w/w |
|---|---|
| Xanthan gum (Thew Arnott) | 0.50 |
| $NaH_2PO_4$ (as pH 7.50 phosphate buffer, 50 mM) | 0.60 |
| Demineralised Water | qs to 100% |

| FINAL PRODUCT | % w/w |
|---|---|
| GEL POLYAPHRON DISPERSION 1 | 11.66 |
| GEL POLYAPHRON DISPERSION 2 | 27.54 |
| GEL POLYAPHRON DISPERSION 3 | 50.87 |
| AQUEOUS GEL | 9.93 |

*The Calcipotriol content in the final formulation is 47.0 μg/g.

**The betamethasone dipropionate content in the final formulation is 709 μg/g (equivalent to 551 μg/g of betamethasone).

Manufacturing Method

The method used was precisely as described for Example 1 above except that the neutralised aqueous gel was added to the final mixture of the three gel polyaphron dispersions, 1, 2 and 3 and then mixed in by simple mixing until the product was a homogeneous mixture of the polyaphron dispersions.

Example 6

Three gel polyaphron dispersions and an aqueous gel of the following compositions were prepared by the following method.

| Gel POLYAPHRON DISPERSION 1 | % |
|---|---|
| Oil Phase | |
| Calcipotriol solution* (0.02687%) in isopropyl myristate (Lexol IPM NF - Inolex) | 89.00 |
| Laureth-4 (Volpo L4 - Croda) | 1.00 |
| Aqueous Phase | |
| Poloxamer 188 (Pluronic F68 - BASF) | 1.00 |
| Propan-2-ol | 2.70 |
| Demineralised Water | 5.40 |

| Gel POLYAPHRON DISPERSION 2 | % |
|---|---|
| Oil Phase | |
| Betamethasone Dipropionate solution** (0.3289%) in isopropyl myristate (Lexol IPM NF - Inolex) | 89.00 |
| Laureth-4 (Volpo L4 - Croda) | 1.00 |
| Aqueous Phase | |
| Poloxamer 188 (Pluronic F68 - BASF) | 1.00 |
| Propan-2-ol (Fisher) | 2.70 |
| Demineralised Water | 5.40 |

| Gel POLYAPHRON DISPERSION 3 | % w/w |
|---|---|
| Oil Phase | |
| Squalane (Olive-derived - A & E Connock) | 9.00 |
| Dimethicone (Q7-9120, 100 CP - Dow Corning) | 44.10 |
| Cyclomethicone (ST5NF - Dow Corning) | 36.00 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| AQUEOUS GEL | % w/w |
|---|---|
| Polyacrylic acid (Ultrez 10, Noveon) | 2.00 |
| Propan-2-ol (Fisher) | 30.00 |
| 50% triethanolamine (aq) | to pH 7.29 |
| Demineralised Water | qs to 100% |

| FINAL PRODUCT | % w/w |
|---|---|
| GEL POLYAPHRON DISPERSION 1 | 25.00 |
| GEL POLYAPHRON DISPERSION 2 | 25.00 |
| GEL POLYAPHRON DISPERSION 3 | 40.00 |
| AQUEOUS GEL | 10.00 |

*The Calcipotriol content in the final formulation is 67.9 μg/g.

**The betamethasone dipropionate content in the final formulation is 783 μg/g (equivalent to 609 μg/g of betamethasone).

Manufacturing Method

The method used was as described for Example 1 above except that the neutralised aqueous gel was added to the final mixture of the three gel polyaphron dispersions, 1, 2 and 3 and then mixed in by simple mixing until the product was a homogeneous mixture of the polyaphron dispersions.

Stability Measurements

Stability was tested as in Example 1a, the sample was stored in close-sealed eppendorf tubes.

The inventors observed that after 3 months storage at 40° C. the levels of calcipotriol and betamethasone were 101% and 106% of the original levels respectively. Stability testing is ongoing with this sample.

Furthermore, after 6 months storage at 40° C. the levels of calcipotriol and betamethasone were 107% and 100% of the original levels respectively.

Example 7

Three gel polyaphron dispersions and an aqueous gel of the following compositions were prepared by the following method.

| Gel POLYAPHRON DISPERSION 1 | % |
|---|---|
| Oil Phase | |
| Calcipotriol solution* (0.0258% in isopropyl myristate (Lexol IPM NF - Inolex) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 2 | |
|---|---|
| | % |
| Oil Phase | |
| Betamethasone Dipropionate solution** (0.325%) in isopropyl myristate (Lexol IPM NF - Inolex) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 3 | |
|---|---|
| | % w/w |
| Oil Phase | |
| Squalane (Olive-derived - A & E Connock) | 20.00 |
| Dimethicone (Q7-9120, 20 cSt - Dow Corning) | 35.00 |
| Elastomer DC10 (Dow Corning) | 5.00 |
| Cyclomethicone (STb5NF - Dow Corning) | 26.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| AQUEOUS GEL | |
|---|---|
| | % w/w |
| Polyacrylic acid (Carbomer ETD 2020, supplier) | 2.00 |
| Disodium ethylenediaminetetracetic acid ($Na_2$ EDTA, Fisher) | 0.20 |
| Sodium bisulphite ($NaHSO_3$, Fisher) | 0.50 |
| NaOH 20% aqueous solution | To pH 7.71 |
| Demineralised Water | qs to 100% |

| FINAL PRODUCT | % w/w |
|---|---|
| GEL POLYAPHRON DISPERSION 1 | 25.00 |
| GEL POLYAPHRON DISPERSION 2 | 25.00 |
| GEL POLYAPHRON DISPERSION 3 | 20.00 |
| AQUEOUS GEL | 30.00 |

*The Calcipotriol content in the final formulation is 57.4 µg/g.

**The betamethasone dipropionate content in the final formulation is 723 µg/g (equivalent to 562 µg/g of betamethasone).

Manufacturing Method

The method used was as described for Example 1 above except that the neutralised aqueous gel was added to the final mixture of the three gel polyaphron dispersions, 1, 2 and 3 and then mixed in by simple mixing until the product was a homogeneous mixture of the polyaphron dispersions.

Stability Measurements

Stability was tested as in Example 1a, the sample was stored in close-sealed eppendorf tubes.

The inventors observed that after 3 months storage at 40° C. the levels of calcipotriol and betamethasone were 96% and 103% of the original levels respectively. Stability testing is ongoing with this sample. Further stability testing after 6 months storage at 40° C. indicated levels of calcipotriol and betamethasone were 96% and 103% of the original levels respectively.

Example 8

Commercial product (Dovobet (LEO Pharma), lot No EA5525). Dovobet is a commercial product which is also sold under the name Daivobet and Taclonex.

| Product | Ingredients (not in order of concentration | Feel on Skin |
|---|---|---|
| Example 1 U.S. Pat. No. 6,753,013 B1 | 1. Betamethasone dipropionate<br>2. Calcipotriol (Hydrate),<br>3. Polyoxypropylene-15-Stearyl Ether,<br>4. α-Tocopherol,<br>5. White Soft Paraffin | Very sticky and greasy |
| Dovobet (as known as Daivobet, Taclonex) | 1. Betamethasone dipropionate<br>2. Calcipotriol (Hydrate),<br>3. Polyoxypropylene-15-Stearyl Ether,<br>4. α-Tocopherol,<br>5. White Soft Paraffin | Very sticky and greasy |

A sample of the commercial product was stored in a sealed glass jar and stored at 40° C., in the same manner as the Examples above.

After 3 months, the sample was analysed using the extraction method as used for Example 1. Assay using HPLC (as above) indicated drug levels 91% and 70% for calcipotriol and BDP, respectively, compared with analyses performed on fresh sample.

Example 9

Single gel polyaphron dispersion of the following compositions was prepared by the following method.

| Gel POLYAPHRON DISPERSION | |
|---|---|
| | % |
| Oil Phase | |
| Solution of Calcipotriol* (0.0133%) and BDP (0.1554%) in Caprylic/Capric Triglyceride (Mygliol 812 - Condea) | 90.00 |
| Aqueous Phase | |
| Poloxamer 188 (Pluronic F68 - BASF) | 1.00 |
| NaOH solution (20% w/w) | to pH 8.50 |
| Demineralised Water | qs to 9.00 |

*The Calcipotriol content in the final formulation is 120 µg/g.

**The betamethasone dipropionate content in the final formulation is 1399 µg/g (equivalent to 1088 µg/g of betamethasone).

Manufacturing Method

The polyaphron dispersion was made by the method outlined in Example 1.

Stability Measurements

Stability measurements made using the method outlined in Example 1b.

The inventors observed that after storage for 1 month at 40° C. in a sealed glass jar, the formulation had separated into a system with a significant oil phase on top of the polyaphron gel. For the sample stored at ambient temperature after 18 months the levels of calcipotriol and betamethasone were 97%±3% and 98%±3% of the original levels, respectively.

Example 10

| Gel POLYAPHRON DISPERSION 1 | |
|---|---|
| | % |
| Oil Phase | |
| Calcipotriol solution* (0.0671%) in Caprylic/Capric Triglyceride (Mygliol 812 - Condea) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 2 | |
|---|---|
| | % |
| Oil Phase | |
| Betamethasone Dipropionate solution** (0.3294%) in a 3:2 w/w blend of isopropyl myristate (Lexol IPM NF - Inolex):Caprylic/Capric Triglyceride (Mygliol 812 - Condea) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 3 | |
|---|---|
| | % w/w |
| Oil Phase | |
| Squalane (Olive-derived - A & E Connock) | 9.00 |
| Dimethicone (Q7-9120, 100 CP - Dow Corning) | 44.10 |
| Cyclomethicone (STb5NF - Dow Corning) | 36.00 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| AQUEOUS GEL | |
|---|---|
| | % w/w |
| Polyacrylic acid (Ultrez 10 - Noveon) | 1.00 |
| Triethanolamine (TEA) | to pH 7.00 |
| Demineralised Water | qs to 100% |

| FINAL PRODUCT | % w/w |
|---|---|
| GEL POLYAPHRON DISPERSION 1 | 8.89 |
| GEL POLYAPHRON DISPERSION 2 | 23.35 |
| GEL POLYAPHRON DISPERSION 3 | 57.81 |
| Aqueous gel | 9.95 |

* final calcipotriol level 53.2 μg/g
** final BDP level 692 μg/g (equivalent to 538 μg/g betamethasone)

Manufacturing Method

The method used was precisely as described for Example 1 above except that the neutralised aqueous gel was added to the final mixture of the three gel polyaphron dispersions, 1, 2 and 3 and then mixed in by simple mixing until the product was a homogeneous mixture of the polyaphron dispersions.

Stability Measurements

Stability was tested as in Example 1b

The inventors observed that after 2 months storage at 40° C. in a sealed glass jar the levels of calcipotriol and betamethasone dipropionate were 103±2% and 106±3% of the original levels respectively. Furthermore, after 6 months storage at 40° C. the levels of calcipotriol and betamethasone dipropionate were 106±2% and 105±3% of the original levels respectively. Stability testing is ongoing with this sample.

Example 11

Three gel polyaphron dispersions and an aqueous gel of the following compositions were prepared by the following method.

| Gel POLYAPHRON DISPERSION 1 | |
|---|---|
| | % |
| Oil Phase | |
| Calcipotriol solution* (0.0581%) in Caprylic/Capric Triglyceride (Mygliol 812 - Condea) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 2 | |
|---|---|
| | % |
| Oil Phase | |
| Betamethasone Dipropionate solution** (0.2908%) in a 3:2 w/w blend of isopropyl myristate (Lexol IPM NF - Inolex):Caprylic/Capric Triglyceride (Mygliol 812 - Condea) | 89.10 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| Gel POLYAPHRON DISPERSION 3 64/59/8 | |
| --- | --- |
| | % w/w |
| Oil Phase | |
| Squalane (Olive-derived - A & E Connock) | 9.00 |
| Dimethicone (Q7-9120, 100 CP - Dow Corning) | 44.10 |
| Cyclomethicone (STb5NF - Dow Corning) | 36.00 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| BUFFER | |
| --- | --- |
| | % w/w |
| Phosphate buffer salts | 1.00 |
| | to pH 7.50 |
| Demineralised Water | qs to 100% |

| FINAL PRODUCT | % w/w |
| --- | --- |
| GEL POLYAPHRON DISPERSION 1 | 10.15 |
| GEL POLYAPHRON DISPERSION 2 | 25.32 |
| GEL POLYAPHRON DISPERSION 3 | 53.54 |
| BUFFER | 10.99 |

*The Calcipotriol content in the final formulation is 52.5 µg/g.

**The betamethasone dipropionate content in the final formulation is 656 µg/g (equivalent to 510 µg/g of betamethasone).

Manufacturing Method

The method used was precisely as described for Example 1 above except that the buffer was added to the final mixture of the three gel polyaphron dispersions, 1, 2 and 0.3 and then mixed in by simple mixing until the product was a homogeneous mixture of the polyaphron dispersions.

Stability Measurements

Stability was tested as in Example 1b

The inventors observed that after 6 months storage at 40° C. in a sealed glass jar the levels of calcipotriol and betamethasone were 106±2% and 105±1% of the original levels respectively.

Example 12

Three gel polyaphron dispersions of the following compositions were prepared by the following method.

| Gel POLYAPHRON DISPERSION 1 | |
| --- | --- |
| | % |
| Oil Phase | |
| Calcipotriol solution* (0.0283%) isopropyl myristate (Lexol IPM NF - Inolex) | 89.10 |
| Laureth-4 (Volpo L4 - Croda) | 0.90 |

| Gel POLYAPHRON DISPERSION 1 | |
| --- | --- |
| | % |
| Aqueous Phase | |
| Calcipotriol solution* (0.0400% in aq phase) 29.6% w/w isopropanol in demineralised water | 9.00 |
| Poloxamer 188 (Pluronic F68 - BASF) | 1.00 |

| Gel POLYAPHRON DISPERSION 2 | |
| --- | --- |
| | % |
| Oil Phase | |
| Betamethasone dipropionate solution** (0.3289%) in isopropyl myristate (Lexol IPM NF - Inolex) | 89.10 |
| Laureth-4 (Volpo L4 - Croda) | 0.90 |
| Aqueous Phase | |
| Betamethasone dipropionate solution** (0.2252%) in 33.8% w/w isopropanol in demineralised water | 9.00 |
| Poloxamer 188 (Pluronic F68 - BASF) | 1.00 |

| Gel POLYAPHRON DISPERSION 3 | |
| --- | --- |
| | % w/w |
| Oil Phase | |
| Squalane (Olive-derived - A & E Connock) | 20.00 |
| Dimethicone (Q7-9120, 20 CP - Dow Corning) | 35.00 |
| Cyclomethicone (STb5NF - Dow Corning) | 29.10 |
| Elastomer DC10 (Dow Corning) | 5.00 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| AQUEOUS GEL | |
| --- | --- |
| | % w/w |
| Polyacrylic acid (Ultrez 10 - Noveon) | 2.00 |
| Triethanolamine (TEA) | to pH 7.29 |
| Demineralised Water | qs to 100% |

| FINAL PRODUCT | % w/w |
| --- | --- |
| GEL POLYAPHRON DISPERSION 1 | 25.00 |
| GEL POLYAPHRON DISPERSION 2 | 25.00 |
| GEL POLYAPHRON DISPERSION 3 | 30.00 |
| AQUEOUS GEL | 20.00 |

*The Calcipotriol content in the final formulation is 72.0 µg/g.

**The betamethasone dipropionate content in the final formulation is 782 µg/g (equivalent to 608 µg/g of betamethasone).

Manufacturing Method

The method used was precisely as described for Example 1, except for the inclusion of gel phase.

Stability Measurements

Stability was tested as in Example 1a.

The inventors observed that after 6 months storage at 40° C. in a sealed eppendorf tube the levels of calcipotriol and betamethasone were 106% and 117% of the original levels respectively. Stability testing is ongoing with this sample.

Example 13

Three gel polyaphron dispersions and an aqueous gel of the following compositions were prepared by the following method.

| Gel POLYAPHRON DISPERSION 1 | % |
|---|---|
| Oil Phase | |
| Calcipotriol solution* (0.0283%) isopropyl myristate (Lexol IPM NF - Inolex) | 89.10 |
| Laureth-4 (Volpo L4 - Croda) | 0.90 |
| Aqueous Phase | |
| Calcipotriol solution* (0.0400% in aq phase) 29.6% w/w isopropanol in demineralised water | 9.00 |
| Poloxamer 188 (Pluronic F68 - BASF) | 1.00 |

| Gel POLYAPHRON DISPERSION 2 | % |
|---|---|
| Oil Phase | |
| Betamethasone dipropionate solution** (0.3289%) in isopropyl myristate(Lexol IPM NF - Inolex) | 89.10 |
| Laureth-4 (Volpo L4 - Croda) | 0.90 |
| Aqueous Phase | |
| Betamethasone dipropionate solution** (0.2252%) in 33.8% w/w isopropanol in demineralised water | 9.00 |
| Poloxamer 188 (Pluronic F68 - BASF) | 1.00 |

| Gel POLYAPHRON DISPERSION 3 | % w/w |
|---|---|
| Oil Phase | |
| Squalane (Olive-derived - A & E Connock) | 20.00 |
| Dimethicone (Q7-9120, 20 CP - Dow Corning) | 35.00 |
| Cyclomethicone (STb5NF - Dow Corning) | 29.10 |
| Elastomer DC10 (Dow Corning) | 5.00 |
| Laureth-4 (Volpo L4 - Croda) | 0.90 |
| Aqueous Phase | |
| Poloxamer 188 (Pluronic F68 - BASF) | 1.00 |
| Demineralised Water | 9.00 |

| AQUEOUS GEL | % w/w |
|---|---|
| Polyacrylic acid (Ultrez 10 - Noveon) | 2.00 |
| Triethanolamine (TEA) | to pH 7.29 |
| Isopropanol (30.6% w/w) in demineralised water | qs to 100% |

| FINAL PRODUCT | % w/w |
|---|---|
| GEL POLYAPHRON DISPERSION 1 | 25.00 |
| GEL POLYAPHRON DISPERSION 2 | 25.00 |
| GEL POLYAPHRON DISPERSION 3 | 20.00 |
| AQUEOUS GEL | 30.00 |

*The Calcipotriol content in the final formulation is 72.0 µg/g.

**The betamethasone dipropionate content in the final formulation is 782 µg/g (equivalent to 608 µg/g of betamethasone).

Manufacturing Method

The method used was precisely as described for Example 1 above except that the neutralised aqueous gel was added to the final mixture of the three gel polyaphron dispersions, 1, 2 and 3 and then mixed in by simple mixing until the product was a homogeneous mixture of the polyaphron dispersions.

Stability Measurements

Stability was tested as in Example 1a

The inventors observed that after 6 month storage at 40° C. in a sealed eppendorf tube the levels of calcipotriol and betamethasone were 104% and 116% of the original levels respectively. Storage stability testing is ongoing.

Example 14

Three gel polyaphron dispersions and an aqueous gel of the following compositions were prepared by the following method.

| Gel POLYAPHRON DISPERSION 1 | % |
|---|---|
| Oil Phase | |
| Calcipotriol solution* (0.0243% w/w) in caprylic capric triglyceride (Mygliol 812 - Condea) | 89.00 |
| Laureth-4 (Volpo L4 - Croda) | 1.00 |
| Aqueous Phase | |
| Calcipotriol solution* (0.0400% w/w) 33.3% w/w isopropanol in demineralised water | 9.00 |
| Poloxamer 188 (Pluronic F68 - BASF) | 1.00 |

| Gel POLYAPHRON DISPERSION 2 | % |
|---|---|
| Oil Phase | |
| Betamethasone dipropionate solution** (0.203% w/w) in caprylic capric triglyceride (Mygliol 812 - Condea) | 89.00 |
| Laureth-4 (Volpo L4 - Croda) | 1.00 |
| Aqueous Phase | |
| Betamethasone dipropionate solution** (0.192% w/w) in 33.3% w/w isopropanol in demineralised water | 9.00 |
| Poloxamer 188 (Pluronic F68 - BASF) | 1.00 |

| Gel POLYAPHRON DISPERSION 3 | |
|---|---|
| | % w/w |
| Oil Phase | |
| Squalane (Olive-derived - A & E Connock) | 19.8 |
| Dimethiconol 20 (- Dow Corning) | 34.60 |
| Cyclomethicone (STb5NF - Dow Corning) | 28.70 |
| Elastomer DC10 (Dow Corning) | 4.90 |
| Laureth-4 (Volpo L4 - Croda) | 1.00 |
| Tween 80 (Polysorbate 80 - Surfachem) | 1.00 |
| Aqueous Phase | |
| Isopropanol | 3.00 |
| Demineralised Water | 6.00 |
| Polyoxyl 40 hydrogenated castor oil (Cremophor RH 40 - BASF) | 1.00 |

| AQUEOUS GEL | |
|---|---|
| | % w/w |
| Polyacrylic acid (Ultrez 10 - Noveon) | 2.00 |
| Triethanolamine (TEA) | to pH 7.29 |
| Isopropanol (30.6% w/w) in demineralised water | qs to 100% |

| FINAL PRODUCT | % w/w |
|---|---|
| GEL POLYAPHRON DISPERSION 1 | 15.00 |
| GEL POLYAPHRON DISPERSION 2 | 27.00 |
| GEL POLYAPHRON DISPERSION 3 | 40.00 |
| AQUEOUS GEL | 18.00 |

*The Calcipotriol content in the final formulation is 37.8 µg/g.

**The betamethasone dipropionate content in the final formulation is 534 µg/g (equivalent to 415 µg/g of betamethasone).

Manufacturing Method

The method used was precisely as described for Example 1 above except that the neutralised aqueous gel was added to the final mixture of the three gel polyaphron dispersions, 1, 2 and 3 and then mixed in by simple mixing until the product was a homogeneous mixture of the polyaphron dispersions.

Stability Measurements

Stability was tested as in Example 1a

The inventors observed that after 3.5 weeks storage at 40° C. in a sealed eppendorf tube the levels of calcipotriol and betamethasone dipropionate were 99% and 138% of the original levels respectively. Storage stability testing is ongoing.

Example 15

Three gel polyaphron dispersions and an aqueous gel of the following compositions were prepared by the following method.

| Gel POLYAPHRON DISPERSION 1 | |
|---|---|
| | % |
| Oil Phase | |
| Calcipotriol solution* (0.0243% w/w) in caprylic capric triglyceride (Mygliol 812 - Condea) | 89.00 |
| Laureth-4 (Volpo L4 - Croda) | 1.00 |
| Aqueous Phase | |
| Calcipotriol solution* (0.0400% w/w) 33.3% w/w isopropanol in demineralised water | 9.00 |
| Poloxamer 188 (Pluronic F68 - BASF) | 1.00 |

| Gel POLYAPHRON DISPERSION 2 | |
|---|---|
| | % |
| Oil Phase | |
| Betamethasone dipropionate solution** (0.203% w/w) in caprylic capric triglyceride (Mygliol 812 - Condea) | 89.00 |
| Laureth-4 (Volpo L4 - Croda) | 1.00 |
| Aqueous Phase | |
| Betamethasone dipropionate solution** (0.192% w/w) in 33.3% w/w isopropanol in demineralised water | 9.00 |
| Poloxamer 188 (Pluronic F68 - BASF) | 1.00 |

| Gel POLYAPHRON DISPERSION 3 | |
|---|---|
| | % w/w |
| Oil Phase | |
| Squalane (Olive-derived - A & E Connock) | 19.8 |
| Dimethiconol 20 (- Dow Corning) | 34.60 |
| Cyclomethicone (STb5NF - Dow Corning) | 28.70 |
| Elastomer DC10 (Dow Corning) | 4.90 |
| Laureth-4 (Volpo L4 - Croda) | 1.00 |
| Tween 80 (Polysorbate 80 - Surfachem) | 1.00 |
| Aqueous Phase | |
| Isopropanol | 3.00 |
| Demineralised Water | 6.00 |
| Polyoxyl 40 hydrogenated castor oil (Cremophor RH 40 - BASF) | 1.00 |

| AQUEOUS GEL | |
|---|---|
| | % w/w |
| Polyacrylic acid (Ultrez 10 - Noveon) | 2.00 |
| Triethanolamine (TEA) | to pH 7.29 |
| Isopropanol (30.6% w/w) in demineralised water | qs to 100% |

| FINAL PRODUCT | % w/w |
|---|---|
| GEL POLYAPHRON DISPERSION 1 | 15.00 |
| GEL POLYAPHRON DISPERSION 2 | 27.00 |
| GEL POLYAPHRON DISPERSION 3 | 30.00 |
| AQUEOUS GEL | 28.00 |

*The Calcipotriol content in the final formulation is 37.8 µg/g.

**The betamethasone dipropionate content in the final formulation is 534 μg/g (equivalent to 415 μg/g of betamethasone).

Manufacturing Method

The method used was precisely as described for Example 1 above except that the neutralised aqueous gel was added to the final mixture of the three gel polyaphron dispersions, 1, 2 and 3 and then mixed in by simple mixing until the product was a homogeneous mixture of the polyaphron dispersions.

Stability Measurements

Stability was tested as in Example 1a

The inventors observed that after 3.5 weeks storage at 40° C. in a sealed eppendorf tube the levels of calcipotriol and betamethasone were 95% and 136% of the original levels respectively. Storage stability testing is ongoing.

Example 16

Three gel polyaphron dispersions and an aqueous gel of the following compositions were prepared by the following method.

| Gel POLYAPHRON DISPERSION 1 | % |
|---|---|
| Oil Phase | |
| Calcipotriol solution* (0.0243% w/w) in caprylic capric triglyceride (Mygliol 812 - Condea) | 89.00 |
| Laureth-4 (Volpo L4 - Croda) | 1.00 |
| Aqueous Phase | |
| Calcipotriol solution* (0.0400% w/w) 33.3% w/w isopropanol in demineralised water | 9.00 |
| Poloxamer 188 (Pluronic F68 - BASF) | 1.00 |

| Gel POLYAPHRON DISPERSION 2 | % |
|---|---|
| Oil Phase | |
| Betamethasone dipropionate solution** (0.203% w/w) in caprylic capric triglyceride (Mygliol 812 - Condea) | 89.00 |
| Laureth-4 (Volpo L4 - Croda) | 1.00 |
| Aqueous Phase | |
| Betamethasone dipropionate solution** (0.192% w/w) in 33.3% w/w isopropanol in demineralised water | 9.00 |
| Poloxamer 188 (Pluronic F68 - BASF) | 1.00 |

| Gel POLYAPHRON DISPERSION 3 | % w/w |
|---|---|
| Oil Phase | |
| Squalane (Olive-derived - A & E Connock) | 19.8 |
| Dimethiconol 20 (- Dow Corning) | 34.60 |
| Cyclomethicone (STb5NF - Dow Corning) | 28.70 |
| Elastomer DC10 (Dow Corning) | 4.90 |
| Laureth-4 (Volpo L4 - Croda) | 1.00 |
| Tween 80 (Polysorbate 80 - Surfachem) | 1.00 |
| Aqueous Phase | |
| Isopropanol | 3.00 |
| Demineralised Water | 6.00 |

| Gel POLYAPHRON DISPERSION 3 | % w/w |
|---|---|
| Polyoxyl 40 hydrogenated castor oil (Cremophor RH 40 - BASF) | 1.00 |

| AQUEOUS GEL | % w/w |
|---|---|
| Polyacrylic acid (Ultrez 10 - Noveon) | 2.00 |
| Triethanolamine (TEA) | to pH 7.29 |
| Isopropanol (30.6% w/w) in demineralised water | qs to 100% |

| FINAL PRODUCT | % w/w |
|---|---|
| GEL POLYAPHRON DISPERSION 1 | 15.80 |
| GEL POLYAPHRON DISPERSION 2 | 27.10 |
| GEL POLYAPHRON DISPERSION 3 | 19.70 |
| AQUEOUS GEL | 37.40 |

*The Calcipotriol content in the final formulation is 39.9 μg/g.

**The betamethasone dipropionate content in the final formulation is 536 μg/g (equivalent to 417 μg/g of betamethasone).

Manufacturing Method

The method used was precisely as described for Example 1 above except that the neutralised aqueous gel was added to the final mixture of the three gel polyaphron dispersions, 1, 2 and 3 and then mixed in by simple mixing until the product was a homogeneous mixture of the polyaphron dispersions.

Stability Measurements

Stability was tested as in Example 1a

The inventors observed that after 3.5 weeks storage at 40° C. in a sealed eppendorf tube the levels of calcipotriol and betamethasone were 101% and 137% of the original levels respectively. Storage stability testing is ongoing.

SUMMARY

| ID | storage medium | stability (time) |
|---|---|---|
| Example 1 | Glass | 2 months (ongoing) |
| Example 1 | Plastic | 2 months[a] |
| Example 2 | Glass | 2 months* (ongoing) |
| Example 3 | Glass | 9 months |
| Example 4 | Glass | 4.5 months** |
| Example 5 | Glass | ongoing |
| Example 6 | Plastic | 3 months (ongoing) |
| Example 7 | Plastic | 3 months*** |
| Example 8 | Glass | 3 months**** Unstable |
| Example 9 | Glass | 18 months at room temp |
| Example 10 | Glass | 6 months |
| Example 11 | Glass | 6 months |
| Example 12 | Plastic | 6 months |
| Example 13 | Plastic | 6 months |
| Example 14 | Plastic | 3.5 weeks |

| ID | storage medium | stability (time) |
| --- | --- | --- |
| Example 15 | Plastic | 3.5 weeks |
| Example 16 | Plastic | 3.5 weeks |

Stability as defined above; less than 5% loss of either drug compared with initial drug levels. Storage at 40° C., unless otherwise stated.
<sup>a</sup>levels of calcipotriol and betamethasone dipropionate 102% and 99% of original levels
*Level of betamethasone = 95% of original in latest storage sample.
**After 6 months, levels of calcipotriol and betamethasone dipropionate were 42% and 65% of original, respectively.
***Level of calcipotriol = 86% of original after 4 months at 40° C.
****After 3 months, levels of calcipotriol and betamethasone dipropionate were 91% and 70% of original, respectively.

The invention claimed is:

1. An aqueous composition suitable for topical application comprising:
a polyaphron dispersion comprising one or more surfactant, a continuous phase, and a discontinuous phase, wherein the continuous phase comprises water and the discontinuous phase comprises a pharmaceutically acceptable oil that is immiscible or substantially immiscible with the continuous phase, wherein the discontinuous phase comprises droplets, and wherein the droplets are dispersed in the continuous phase;
wherein the composition comprises 5% to 90% by weight of the water based on the total weight of the aqueous composition;
wherein the polyaphron dispersion further comprises (i) at least one of vitamin D or vitamin D analogue, and (ii) at least one corticosteroid;
wherein the (i) at least one of vitamin D or vitamin D analogue, and the (ii) at least one of corticosteroid are predominantly in the droplets.

2. An aqueous composition according to claim 1, wherein the corticosteroid comprises betamethasone, clobetasol, clobetasone, desoximethasone, diflucortolon, difluorasone, fluocinoid, flumethasone, fluocinolon, fluticasone, fluprednidene, halcinonide, hydrocortisone, momethasone, triamcinolon, and their esters, or mixture thereof.

3. An aqueous composition according to claim 1, wherein the vitamin D or vitamin D analogue comprises vitamin D, calcipotriol, seocalcitol, calcitriol, tacalcitol, maxacalcitol, paricalcitol, falecalcitriol, 1a,24S-dihydroxy-vitamin D2, 1(S), 3(R)-dihydroxy-20(R)-[((3-(2-hydroxy-2-propyl)-phenyl)-methoxy)-methyl]-9,10-seco-pregna-5 (Z), 7(E), 10 (19)-triene, or a mixture thereof.

4. An aqueous composition according to claim 1, wherein the oil comprises monoglyceride, diglyceride, triglyceride, isopropyl myristate, or mixture thereof.

5. An aqueous composition according to claim 1, wherein the composition comprises at least 10% by weight of the water based on the total weight of the aqueous composition.

6. An aqueous composition according to claim 1, wherein the composition comprises at least 15% by weight of the water based on the total weight of the aqueous composition.

7. An aqueous composition according to claim 1, wherein the composition comprises 5 to 50% by weight of the water based on the total weight of the aqueous composition.

8. An aqueous composition according to claim 1, wherein the aqueous composition has a pH of 7.0 to 8.5.

9. An aqueous composition according to claim 1, wherein the aqueous composition has a pH of 7.25 to 7.75.

10. An aqueous composition according to claim 1, wherein the continuous phase comprises xanthane gum, or isopropyl alcohol and neutralized polyacrylic acid.

11. An aqueous composition according to claim 1, wherein the continuous phase comprises a compound of formula $R_1$—OH where $R_1$ is $C_1$-$C_{10}$ alkyl and/or a compound of formula HO—$R_2$—H where $R_2$ is $(C_2H_4)_n$ or $(C_3H6)$ n where n is 1 to 100.

12. An aqueous composition according to claim 11, wherein the continuous phase comprises propylene glycol, glycerol, ethanol, isopropyl alcohol, or a mixture thereof.

13. An aqueous composition according to claim 1, further comprising a gelling agent.

14. An aqueous composition according to claim 1, further comprising a permeation enhancer.

15. An aqueous composition according to claim 1, wherein the aqueous composition comprises from 60 to 95% by weight of the at least one discontinuous phase.

16. An aqueous composition according to claim 1, wherein the aqueous composition comprises from 5 to 40% by weight of the continuous phase.

17. An aqueous composition according to claim 1, wherein the composition provides no more than a 5% reduction in the amount of the vitamin D or vitamin D analogue and no more than a 5% reduction in the amount of the corticosteroid with respect to the original amounts after three months of storage in a sealed glass container at 40° C.

18. An aqueous composition according to claim 1, wherein the at least one vitamin D or vitamin D analogue comprises calcipotriol.

19. An aqueous composition according to claim 1, wherein the at least one corticosteroid comprises betamethasone.

* * * * *